US008137936B2

(12) United States Patent
Macevicz

(10) Patent No.: US 8,137,936 B2
(45) Date of Patent: Mar. 20, 2012

(54) SELECTED AMPLIFICATION OF POLYNUCLEOTIDES

(76) Inventor: Stephen C. Macevicz, Cupertino, CA (US)

( * ) Notice: Subject to any disclaimer, the term of this patent is extended or adjusted under 35 U.S.C. 154(b) by 838 days.

(21) Appl. No.: 11/564,329

(22) Filed: Nov. 29, 2006

(65) Prior Publication Data
US 2007/0128635 A1    Jun. 7, 2007

Related U.S. Application Data

(60) Provisional application No. 60/740,482, filed on Nov. 29, 2005, provisional application No. 60/748,102, filed on Dec. 6, 2005, provisional application No. 60/763,252, filed on Jan. 30, 2006.

(51) Int. Cl.
C12P 19/34    (2006.01)
(52) U.S. Cl. ........................................ 435/91.2
(58) Field of Classification Search .................. None
See application file for complete search history.

(56) References Cited

U.S. PATENT DOCUMENTS

| | | | | |
|---|---|---|---|---|
| 5,439,793 | A | 8/1995 | Rose | 435/6 |
| 5,508,169 | A | 4/1996 | Deugau | 435/6 |
| 5,508,178 | A | 4/1996 | Rose | 435/91.1 |
| 5,595,891 | A | 1/1997 | Rose | 435/91.1 |
| 5,612,199 | A | 3/1997 | Western | 435/91.1 |
| 5,707,807 | A | 1/1998 | Kato | 435/6 |
| 5,710,000 | A | 1/1998 | Sapolsky | 435/6 |
| 5,994,068 | A | 11/1999 | Guilfoyle | 435/6 |
| 6,045,994 | A | 4/2000 | Zabeau | 435/6 |
| 6,228,580 | B1 | 5/2001 | Blumenfeld | 435/6 |
| 6,280,948 | B1 | 8/2001 | Guilfoyle | 435/6 |
| 6,350,580 | B1 * | 2/2002 | Sorge | 435/6 |
| 6,403,319 | B1 | 6/2002 | Lizardi | 435/6 |
| 6,573,051 | B2 | 6/2003 | Alsmadi | 435/6 |
| 6,632,611 | B2 | 10/2003 | Su | 435/91.51 |
| 6,849,404 | B2 | 2/2005 | Park | 435/6 |
| 6,955,901 | B2 | 10/2005 | Schouten | 435/91.1 |
| 6,958,225 | B2 | 10/2005 | Dong | 435/91.2 |
| 7,208,295 | B2 | 4/2007 | Faham | 435/91.1 |
| 2003/0104459 | A1 * | 6/2003 | Faham | 435/6 |
| 2003/0232348 | A1 * | 12/2003 | Jones | 435/6 |
| 2004/0067493 | A1 * | 4/2004 | Matsuzaki | 435/6 |
| 2004/0132056 | A1 * | 7/2004 | Su | 435/6 |
| 2004/0219580 | A1 * | 11/2004 | Dunn | 435/6 |
| 2005/0037356 | A1 * | 2/2005 | Gullberg | 435/6 |
| 2005/0095645 | A1 * | 5/2005 | Jones | 435/6 |
| 2005/0142577 | A1 * | 6/2005 | Jones | 435/6 |
| 2007/0287151 | A1 * | 12/2007 | Linnarsson | 435/6 |

FOREIGN PATENT DOCUMENTS
WO    WO 03/012119    * 2/2003

OTHER PUBLICATIONS

Baner et al, "Signal amplification of padlock probes by rolling circle replication," Nucleic Acids Research, 26: 5073-5078 (1998).*
Broude et al, "Multiplex allele-specific target amplification based on PCR suppression," Proc. Natl. Acad. Sci., 98: 206-211 (2001).
Broude, "Stem-loop oligonucleotides: a robust tool for molecular biology and biotechnology," Trends in Biotechnology, 20: 249 (2002).
Callow et al, "Selective DNA amplification from complex genomes using universal double-sided adapters," Nucleic Acids Research, 32: e21 (2004).
Chalaya et al, "Improving specificity of DNA hybridization-based methods," Nucleic Acids Research, 32: e130 (2004).
Chu et al, "Quantitation of immunoglobulin μ-γ1 heavy chain switch region recombination by a digestion-circularization polymerase chain reaction method," Proc. Natl. Acad. Sci., 89: 6978-6982 (1992).
Collins et al, "Directional cloning of DNA fragments at a large distance from an intial probe: a circularization method," Proc. Natl. Acad. Sci., 81: 6812-6816 (1984).
Dahl et al, "Multiplex amplification enabled by selective circularization of large sets of genomic DNA fragments," Nucleic Acids Research, 33: e71 (2005).
Hsuih et al, "Novel, ligation-dependent PCR assay for detection of hepatitis C virus in serum," J. Clinical Microbiol., 34: 501-507 (1996).
Jordan et al, "Genome complexity reduction for SNP genotyping analysis," Proc. Natl. Acad. Sci., 99: 2942-2947 (2002).
Kandpal et al, "A polymerase chain reaction approach for constructing jumping and linking libraries," Nucleic Acids Research, 18: 3081 (1990).
Kim et al, "DARFA: A novel technique for studying differential gene expression and bacterial comparative genomics," Biochemical Biophysical Research Communications 336: 168-174 (2005).
Prod'hom et al, "A reliable amplification technique for the characterization of genomic DNA sequences flanking insertion sequences," FEMS Microbiology Letters, 158: 75-81 (1998).
Schouten et al, "Relative quantification of 40 nucleic acid sequences by multiplex ligation-dependent probe amplification," Nucleic Acids Research, 30: e57 (2002).

(Continued)

Primary Examiner — Teresa E Strzelecka
Assistant Examiner — Suchira Pande

(57) ABSTRACT

The invention provides methods and compositions for selectively amplifying one or more target polynucleotides in a sample. In one aspect, a plurality of selection oligonucleotides are provided that are capable of simultaneously annealing to separate regions of a target polynucleotide to form a complex that is enzymatically converted into a closed double stranded DNA circle that incorporates the sequence region between the two separate regions. Sequences that fail to form such complexes may be removed by nuclease digestion and the sequences of the remaining DNA circles may be amplified by a variety of techniques, such as rolling circle replication after nicking, PCR amplification after linearization, or the like.

21 Claims, 16 Drawing Sheets

OTHER PUBLICATIONS

Shapero et al, "MARA: a novel approach for highly multiplexes locus-specific SNP genotyping using high-density DNA oligonucleotide arrays," Nucleic Acids Research, 32: e181 (2004).

Stenberg et al, "PieceMaker: selection of DNA fragments for selector-guided multiplex amplification," Nucleic Acids Research, 33: e72 (2005).

* cited by examiner

SELECTED AMPLIFICATION OF POLYNUCLEOTIDES

This application claims priority under the following U.S. provisional patent applications: Ser. No. 60/740,482 filed 29 Nov. 2005; Ser. No. 60/748,102 filed 06 Dec. 2005; and Ser. No. 60/763,252 filed 30 Jan. 2006, each one of which is incorporated by reference in its entirety.

BACKGROUND

Targeted amplification of selected polynucleotide sequences from a complex mixture of nucleic acids is of great interest in many areas, including genetic analysis, microorganism detection, diagnostics, environmental monitoring, and the like. Such amplification provides a number of advantages, including the conservation of scarce sample and the enrichment of sequences to be analyzed or for reducing overall sample complexity for improved analysis by "downstream" analytical techniques. Targeted amplification of multiple sequences has been carried out with conventional multiplex polymerase reaction (PCR), although this form of PCR is usually limited to amplifications of fewer then ten target sequences, e.g., Mackay, Clin. Microbiol. Infect., 10:190-212 (2004). Henegariu et al, Biotechniques, 23:504-511 (1997); Elnifro et al. Clin. Microbiol. Rev., 13:559-570 (2000); Gardner et al, J. Clin. Microbiol., 41: 2417-2427 (2003); Kimata et al, Microbiol. Immunol., 49:485-492 (2005); and the like. More recently, several techniques have been introduced to overcome some of the limitations of conventional multiplex PCR, particularly for simultaneously amplifying numbers of sequences in the range of from several tens to several hundreds, e.g. Dahl et al, Nucleic Acids Research 33: e71 (2005); Broude et al, Proc. Natl. Acad. Sci., 98:206-211 (2001); Shapero et al, Nucleic Acids Research, 32:e181 (2004); Faham et al, U.S. patent publ. 2003/0096291; Faham et al. U.S. patent publ. 2003/0104459; Zabeau et al. U.S. Pat. No. 6,045,994 and the like. However, in each of these methods, trade-offs have been made that make them unsuitable for many circumstances where multiplex amplifications is required. For example, most such methods rely on endonuclease digestion of a nucleic acid sample, which limit ones ability to target the sequences to be amplified, and some methods call for the use of extraordinary long primers, or other ancillary oligonucleotide components, for selecting fragments, that are difficult or expensive to synthesized on a routine basis.

In view of the limitations of current targeted amplification methods, it would be beneficial for many applications if such a method were available that neither relied on endonuclease digestion nor required difficult-to-synthesize components.

SUMMARY OF THE INVENTION

In one aspect, the invention provides methods and compositions for amplifying in the same reaction a plurality of target polynucleotides from a sample. In another aspect, the invention provides methods and compositions for forming closed double stranded DNA circles in the same reaction a plurality of target polynucleotides from a sample, wherein such DNA circles may optionally be amplified. In one aspect, the invention provides a method of forming such DNA circles by a self-sustaining reaction of multiple enzymatic activities. One embodiment of this latter aspect may be implemented with the following steps: (a) providing one or more selection primers for each of the plurality of target polynucleotide so that such one or more selection primers anneal to their respective target polynucleotides whenever present in the sample to form a complex comprising a free 5' strand and a free 3' strand; and (b) combining in a reaction mixture the sample under conditions such that the following enzymatic activities are present: (i) a 5' flap endonuclease activity, (ii) a DNA polymerase lacking strand displacement activity, (iii) a 3' single stranded exonuclease, and (iv) a ligase activity, wherein in the presence of nucleoside triphospates any free 3' strand is digested to form an extendable duplex that is extended by the DNA polymerase activity to the free 5' strand, any free 5' strand adjacent to an extended extendable duplex is cleaved to form a first nick, the annealed selection primer is extended for a 3' end along a target polynucleotide to a 5' end of the selection primer to form a second nick, and the first and second nicks are ligated to form a closed double stranded DNA circle. In one form, said 5' flap endonuclease activity, said DNA polymerase activity, said 3' single stranded exonuclease activity, and said ligase activity are provided by a FEN-1 nuclease, a T4 DNA polymerase, and a ligase.

In accordance with another aspect of the invention, selection primers are annealed to target polynucleotide and extended, after which such extended selection primers are separated from the target polynucleotides, combined with connector oligonucleotides to form complexes that are converted into closed double stranded DNA circles. Preferably, after formation of such circles, the reaction mixture is treated with nucleases that destroy, substantially all oligonucleotides and/or polynucleotides that are not in the form of closed double stranded DNA circles. In one aspect, the invention is a method of forming closed double stranded DNA circles containing selected target polynucleotides.

In still another aspect, the method of the invention is implemented with the following steps: (a) providing one or more selection primers for each of the plurality of target polynucleotides, at least one selection primer for each target polynucleotide having a 3' end with a first sequence region complementary to a predetermined region of the target polynucleotide and a 5' end having a sequence complementary to a 5' end of at least one connector oligonucleotide. (b) annealing and extending at least one selection primer whenever its target polynucleotide is present in the sample to form an extended selection primer, each extended selection primer having a second sequence region downstream of its first sequence region; (c) melting and re-annealing the extended selection primers in the presence of connector oligonucleotides so that for each extended selection primer a complex forms between the extended selection primer and a connector oligonucleotide, wherein the first sequence region of the extended selection primer forms a duplex with the 3' end of the connector oligonucleotide and the second sequence region of the extended selection primer forms a duplex with a 5' end of the connector oligonucleotide; (d) treating the complexes with a DNA polymerase and a ligase to extend the 3' end of each connector oligonucleotide and to extend the 3' end of each extended selection primer to form closed double stranded DNA circle; and (e) amplifying the closed double stranded DNA circles. In one aspect, such complexes form via the following intermolecular duplexes: the 5' end of the extended selection primer forms a duplex with the 5' end of the connector oligonucleotide and the 3' end of the connector oligonucleotide forms a duplex with the second sequence region in the extended selection primer. In another aspect, in the step of treating, the DNA polymerase preferably has 3' exonuclease activity and substantially no strand-displacment activity, such as with T4 DNA polymerase.

In another aspect, the method of the invention can be implemented with the following steps: (a) providing at least one selection primer for each of the plurality of preselected polynucleotides, each selection primer having a 3' end with a first sequence region complementary to a first predetermined region of the target polynucleotide and a 5' end having a sequence complementary to a 5' end of at least one connector oligonucleotide the connector oligonucleotide further having a 3' end complementary to a second sequence region of the target polynucleotide downstream of the first predetermined region; (b) annealing and extending the selection primers to their respective target polynucleotides whenever such polynucleotides are present in the sample to form extended selection primers that extend beyond the second sequence region of the target polynucleotide; (c) melting and re-annealing the extended selection primers in the presence of connector oligonucleotides so that for each extended selection primer a complex forms between the extended selection primer and a connector oligonucleotide; (d) treating the complexes with a DNA polymerase and a ligase to extend the 3' end of each connector oligonucleotide and to extend the 3' end of each extended selection primer to form closed double stranded DNA circles and (e) amplifying the closed double stranded DNA circles.

In a further aspect of the invention, the step of treating includes treating the closed double stranded DNA circles with one or more single stranded nucleases to remove sequences that potentially contribute to background signals or spurious amplifications.

In another aspect, the closed double stranded DNA circles are treated with a restriction endonuclease to form linear double stranded DNA fragments for amplification. In a preferred embodiment, such restriction endonuclease acts on a restriction site disposed between two primer binding sites. In further preference, the linearized double stranded DNAs are amplified by PCR or NASBA.

In still another aspect, the invention provides a method of amplifying a plurality of target polynucleotides in a sample comprising the following steps: (a) providing a first selection primer and a second selection primer for each of the plurality of target polynucleotides, each first selection primer having a 3' end capable of annealing to a first segment of a target polynucleotide and each second selection primer having a 5' end capable of annealing to a second segment of a target polynucleotide, the first segment of each target polynucleotide being upstream of and non-contiguous with at least one second segment of such target polynucleotide, the 5' end of each second selection primer having a 5' phosphate group; (b) annealing first and second selection primers to their respective first and second segments whenever its target polynucleotide is present in the sample and extending and ligating each first selection primer to at least one second selection primer to form extended selection primer; and (c) amplifying the extended selection primers to produce an amplicon of the plurality of target polynucleotides. In a preferred embodiment of this aspect, each of said first segments is separated from its respective said second segment by a distance of at least 50 nucleotides, or by a distance in the range of from 50 to 2000 nucleotides. In another preferred embodiment of this aspect, said plurality of said target polynucleotides in said sample are in a range of from 10 to 100.

In still another aspect, the invention provides a method of selectively amplifying one or more target polynucleotides in a sample comprising the following steps: (a) digesting DNA in the sample with one or more type IIs restriction endonucleases that generate random-end fragments, each random-end fragment having ends characteristic of such fragment; (b) ligating circularizing adaptors to one or more selected random-end fragments, each circularizing adaptor having ends complementary to the ends of a random-end fragment so that double stranded DNA circles are formed; (c) digesting uncircularized DNA; and (d) amplifying the random-end fragments in the double stranded DNA circles to produce one or more amplified target polynucleotides.

The aspects of the present invention for selective amplification provide several advantages over current methods. First, it provides a means of amplifying preselected target polynucleotides without relying on the presence of restriction endonuclease sites, second, it provides a means of amplifying a plurality of polynucleotides in the same reaction mixture, thereby conserving sample materials; and finally, it provides a means for reducing background or spurious amplifications of undesired sequences by forming nuclease-resistant double stranded DNA circles with the preselected target polynucleotides.

DETAILED DESCRIPTION OF THE INVENTION

Figure 1A:
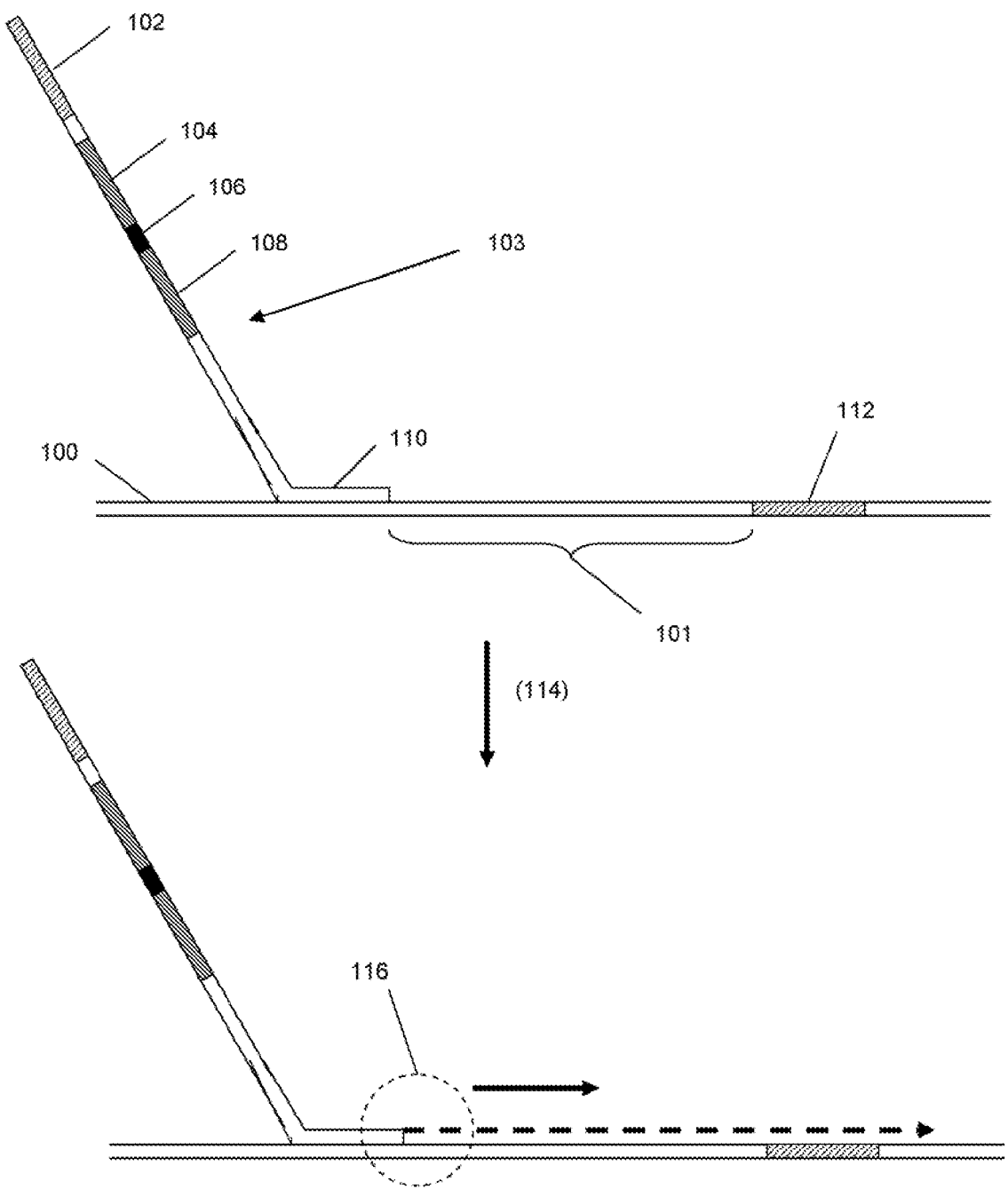
FIGS. 1A-1D illustrate the steps of an embodiment of the invention in which both primers for amplification are in the selection primer.
Figure 1B:
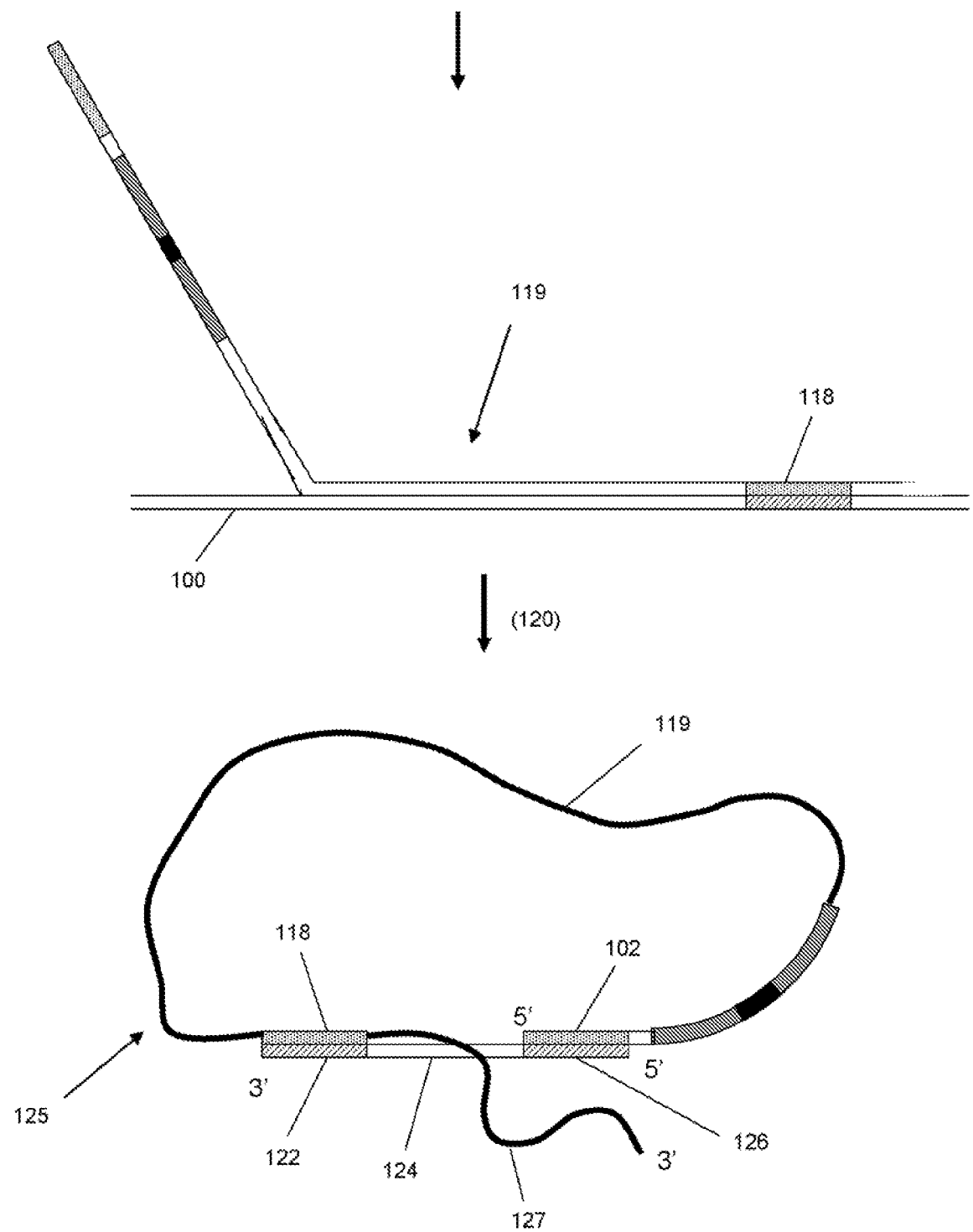
Figure 1C:
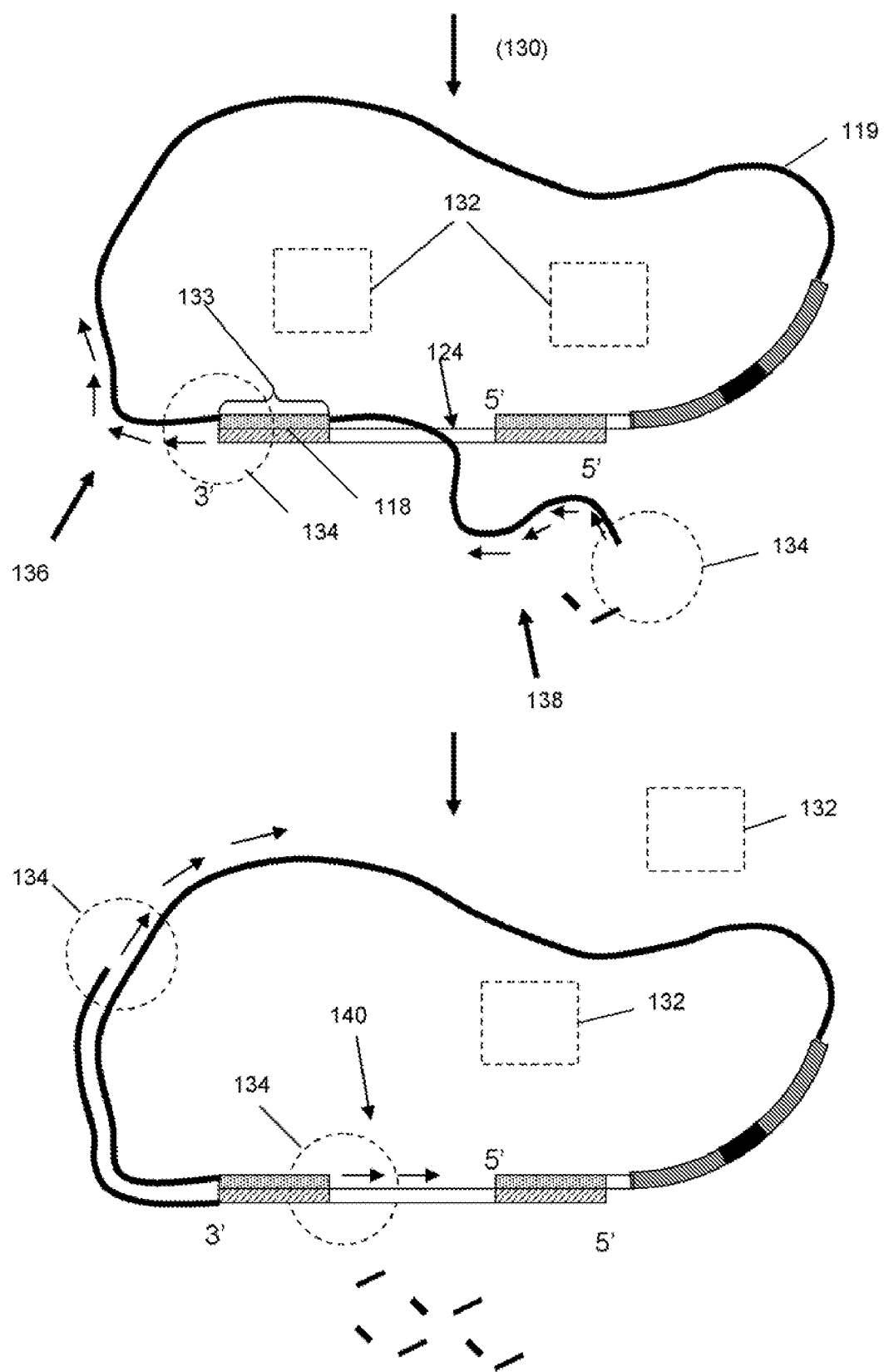
Figure 1D:
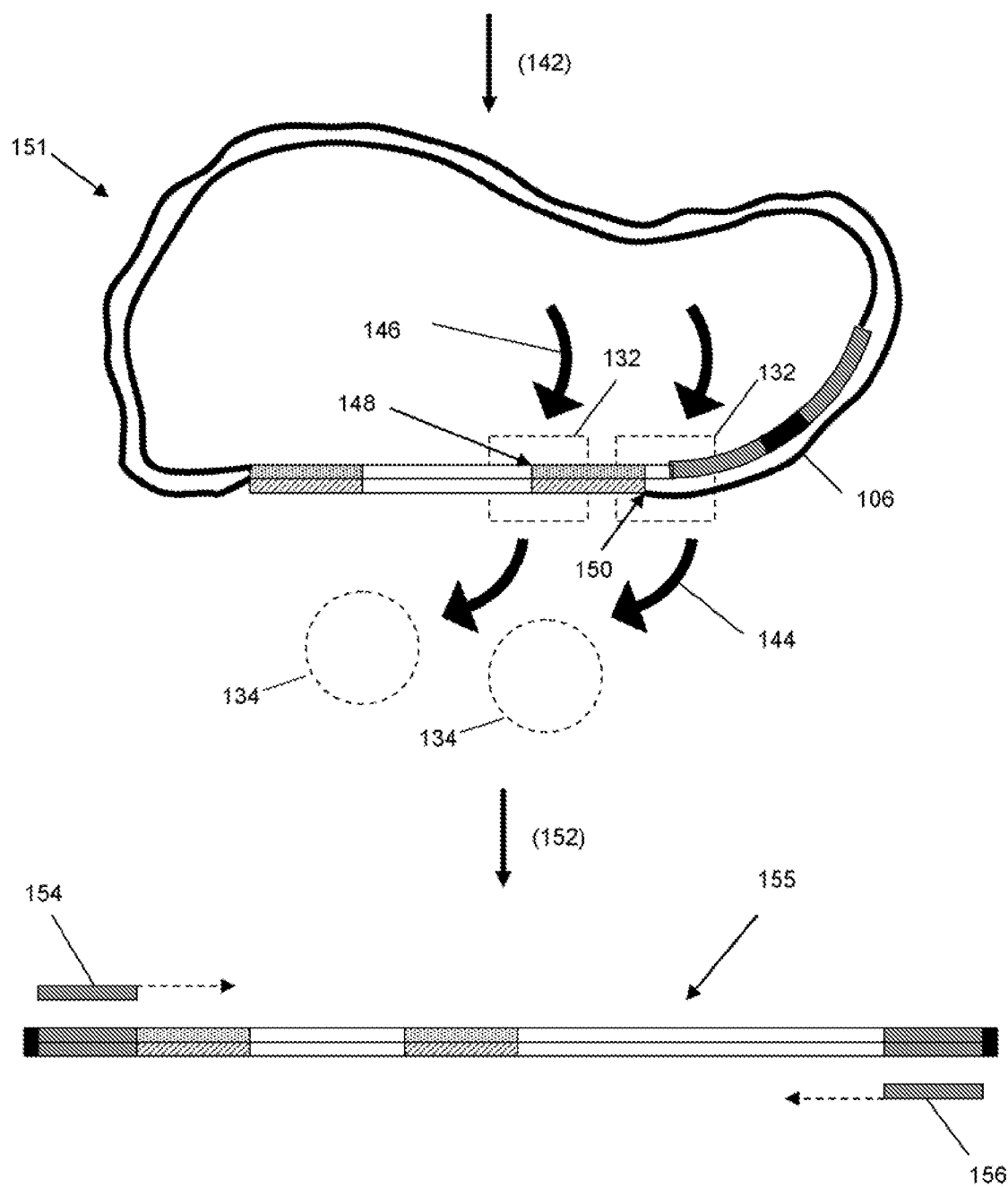
Figure 2A:
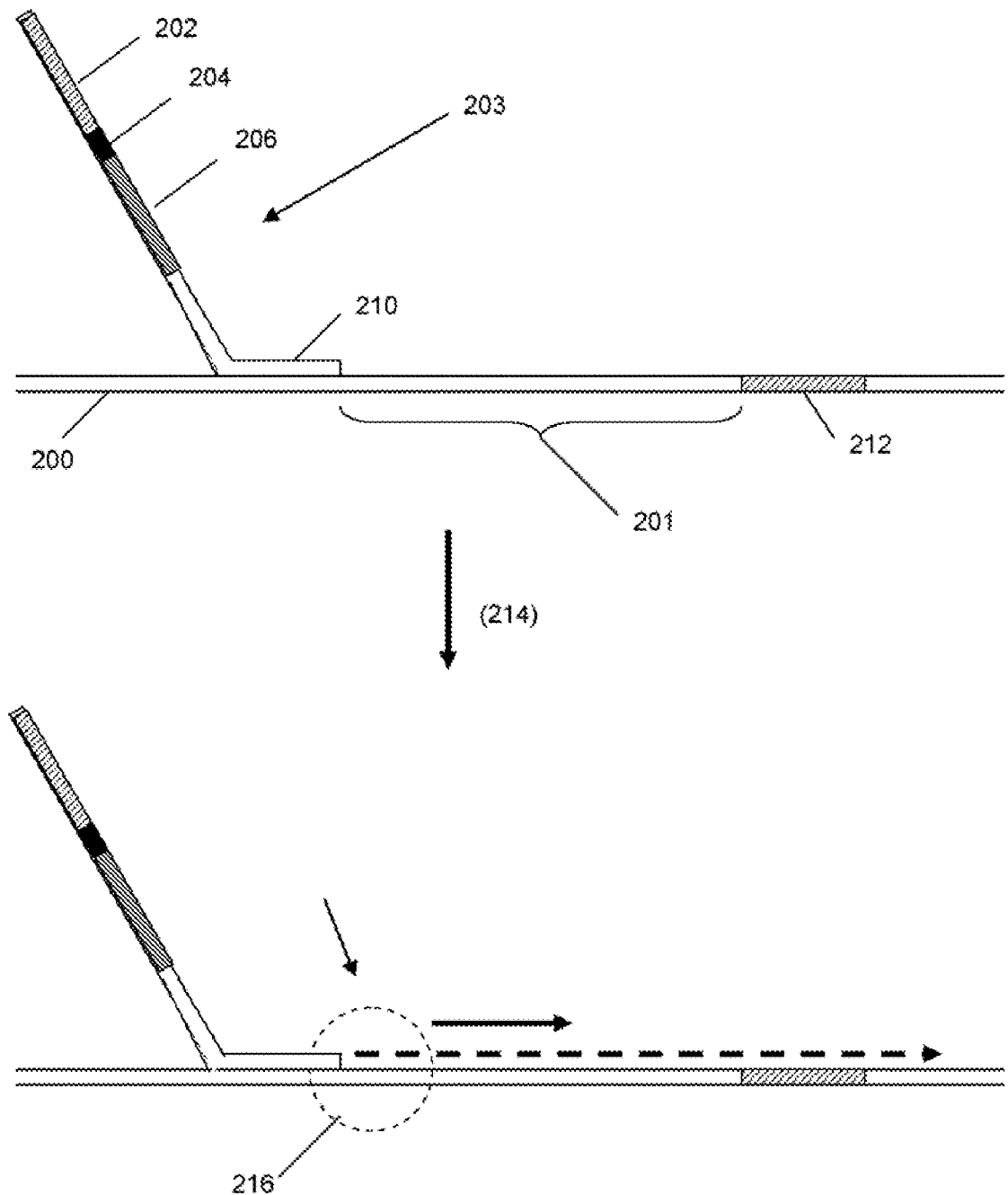
FIGS. 2A-2D illustrate the steps of an embodiment of the invention in which one primer for amplification is in the selection primer and another primer for amplification is in the connector oligonucleotide.
Figure 2B:
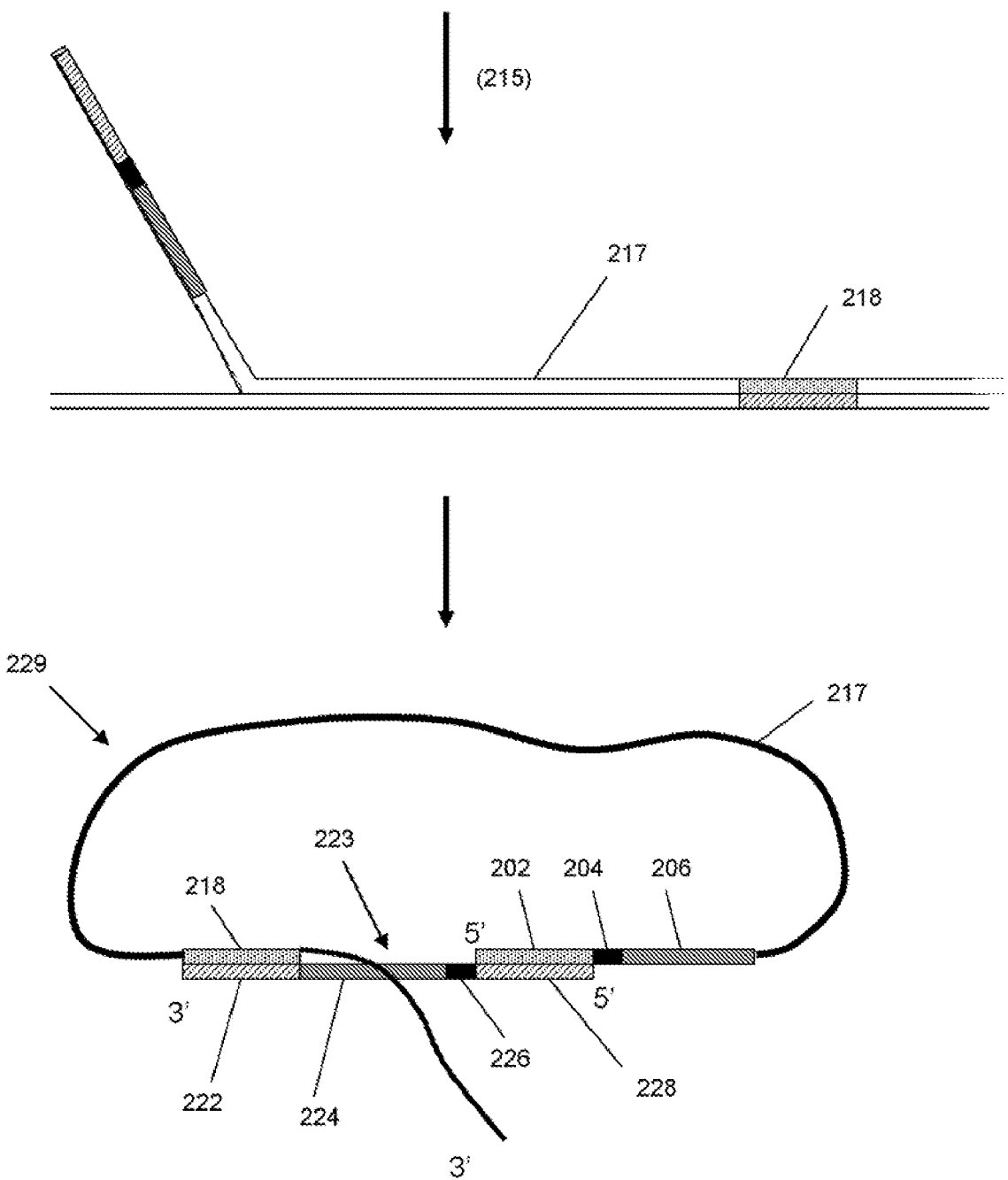
Figure 2C:
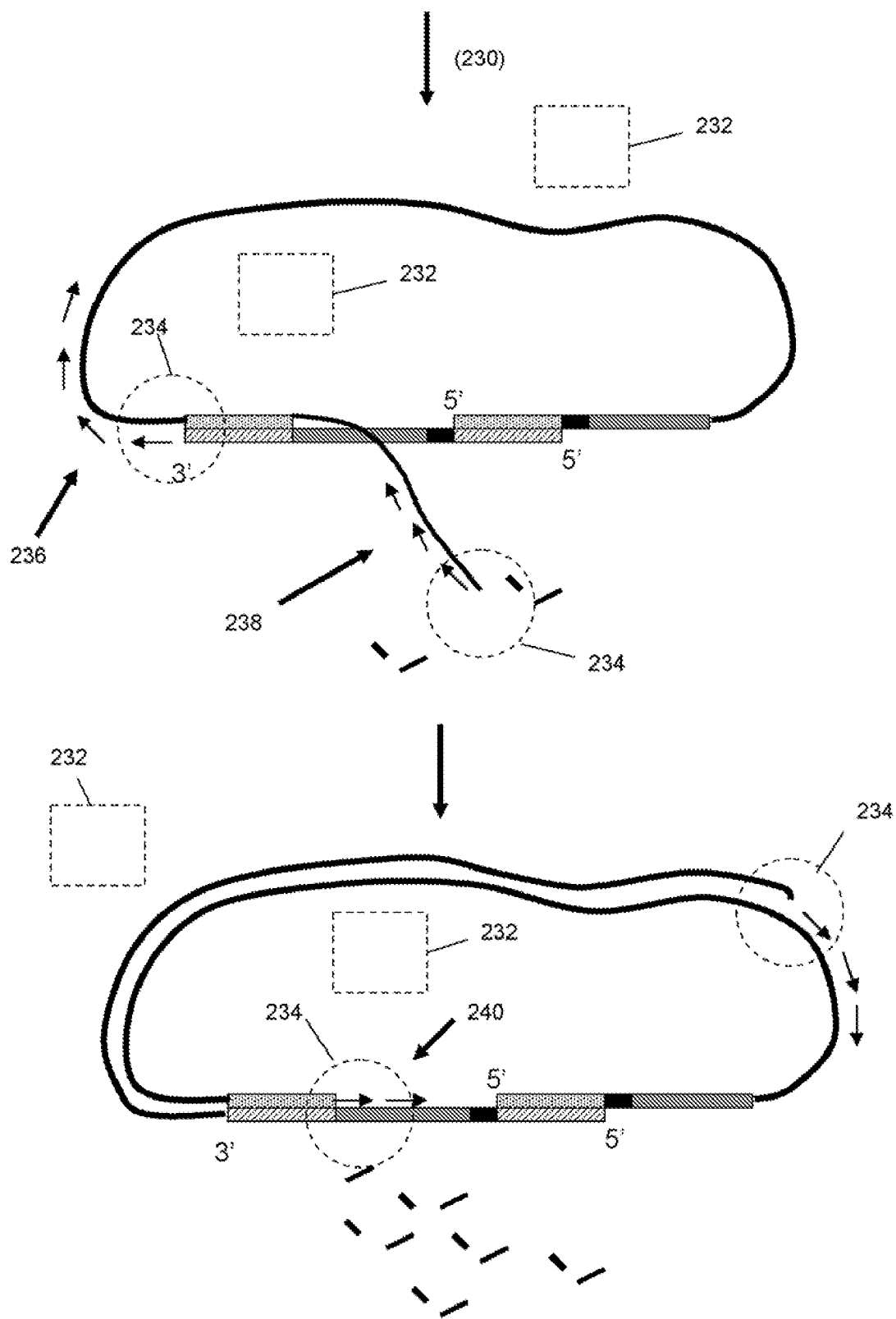
Figure 2D:
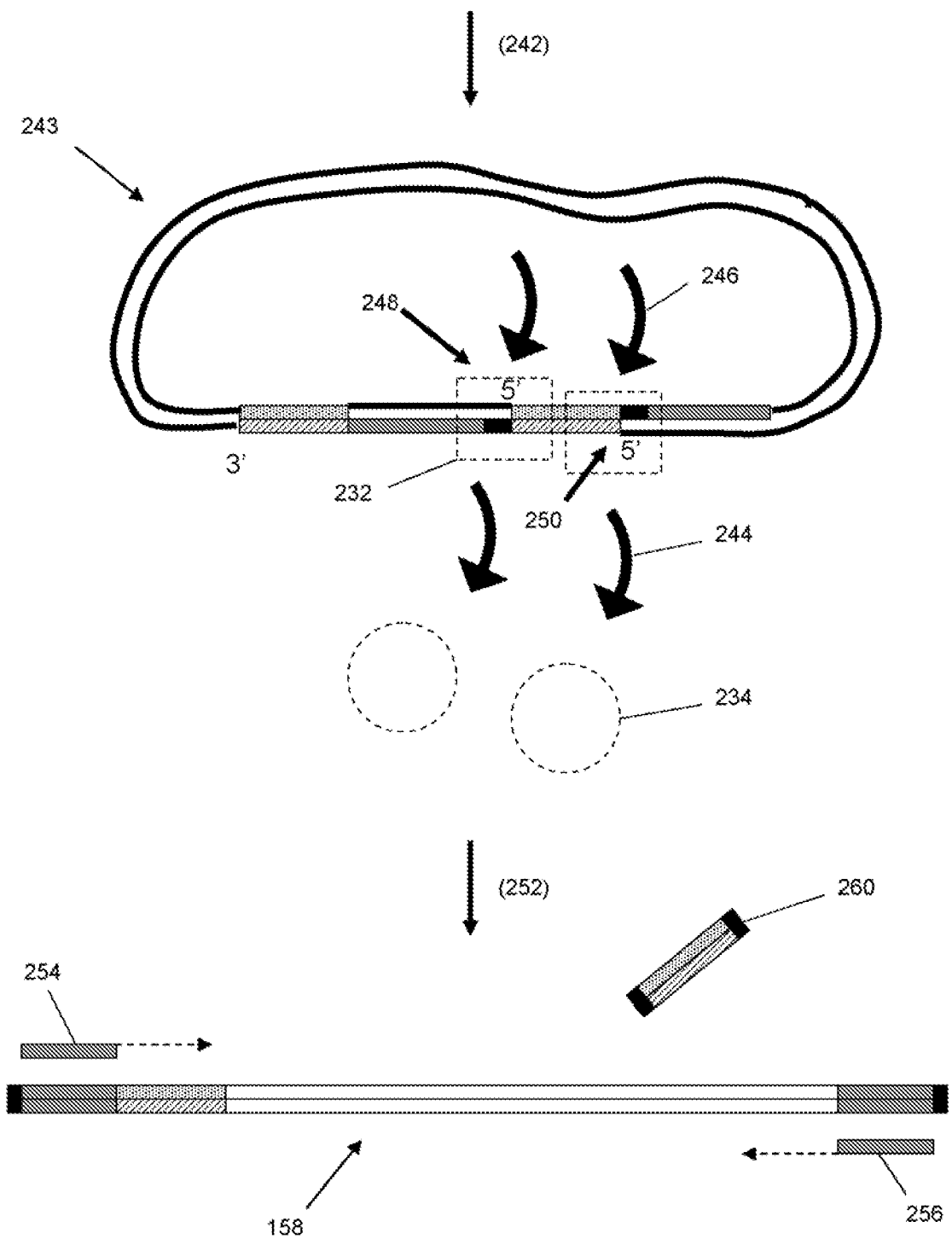

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory, Press), Stryer L. (1995) *Biochemistry* (4th Ed.) Freeman, New York, Gait, *"Oligonucleotide Synthesis: A Practical Approach"* 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry* $5^{th}$ Ed., W. H. Freeman Pub., New York, N.Y., all of which are herein incorporated in their entirety by reference for all purposes.

The invention provides a method of amplifying selected sets of polynucleotides, such as messenger RNAs (mRNAs), complementary DNAs (cDNAs), genomic DNA fragments, and the like. Usually, prior or during the application of the method, such polynucleotides are rendered single stranded if they are present in a sample as double stranded molecules. Polynucleotides for amplification are selected by choosing selection primers that each have a 3' end that anneals to a selected target polynucleotides at a predetermined site. Such selection primers anneal to form extendable duplexes on their respective target polynucleotides. The selection primers each have a 5' end that includes a sequence segment complementary to a 5' end of a connector oligonucleotide and optionally additional sequence segments for use in an amplification reaction. Such additional sequence segments can comprise one or more primer sequences, restriction endonuclease sites, RNA polymerase recognition sites, and the like. In accordance with the method of the invention, after annealing to its respective target polynucleotide, each selection primer is extended with a polymerase to form an extended selection primer. In one aspect, selection primers are extended by a highly processive DNA polymerase, such as Sequence, or like polymerase, to maximize the fidelity of transcription. This is advantageous for applications in which the amplified sequences are compared with standard or references sequences, as for example, in determining somatic mutations in the genes of cancer cells. The newly synthesized portion of an extended selection primer includes a sequence region complementary to a predetermined portion of the target polynucleotide. This complementary region determines the length of the amplicon produced from the target polynucleotide. That is, one end of such amplicon is determined by the site at which the selection primer anneals and the other end is determined by the location of the above complementary region in the extended portion of the extended selection primer. The length and positioning of such complementary region may vary widely. Typically, the selection of such complementary region depends on (i) balancing and/or annealing temperatures among the plurality of target polynucleotides to be amplified, (ii) the desired length of the resulting amplicon, (iii) the need to ensure that the set of such complementary regions are sufficiently different from one another to minimize cross hybridization, (iv) the ability to synthesize long oligonucleotides, and the like.

After such extended selection primers are formed, the resulting duplexes are denatured and then renatured in the presence of connector oligonucleotides. In one aspect, such connector oligonucleotides are provided in substantial molar excess in order to drive the formation of complexes comprising an extended selection primer and its corresponding connector oligonucleotide. Such molar excess can be a 100-fold excess; or in another aspect, can be a 25-fold excess; or in another aspect, it can be a 10-fold excess; or it may be a 5-fold excess. In another aspect, whenever the polymerase used to form extended selection primers has strand displacement activity, after formation of the extended selection primers, such polymerase is denatured, so that such displace activity does not reduce the efficiency of subsequent steps as described more fully below. In a complex that forms between an extended selection primer and its corresponding connector oligonucleotides, the 5' end of the connector oligonucleotide forms a duplex with the 5' end of the selection primer and the 3' end of the connector oligonucleotide forms a duplex with the sequence in the extended portion of the extended selection primer that is complementary to a predetermined segment of the target polynucleotide, described above. In one aspect, the latter duplex is extendable with a DNA polymerase. Such complexes are treated with a combination of a DNA polymerase and a DNA ligase. Such treatment may be sequential, that is, application of a DNA polymerase followed by application of a ligase; or such treatment may include application of both a DNA polymerase and a ligase at the same time. In one aspect as mentioned above, the DNA polymerase lacks strand displacement activity. In another aspect, the DNA polymerase possesses 3'→5' single stranded DNA exonuclease activity. Preferably, such DNA polymerase is T4 DNA polymerase, or like enzyme. After such treatment, double stranded DNA circles that are formed form the complexes may be amplified in a variety of ways depending on the embodiment in one aspect, prior to amplification, non-circularized nucleic acids are digested, e.g. with one or more single stranded exonucleases and/or endonucleases, to minimize spurious amplification of unintended sequences, thereby reducing background or nonspecific amplifications. Where dsDNA circles contain a promoter site, amplification can be by rolling circle using an RNA polymerase, or such circles can be linearized and amplification can be effected by run-off synthesis of RNA copies of the dsDNA sequence. Alternatively, dsDNA circles can contain a recognition site for a nicking enzyme, such as N.Alw I, N.BstNB I, N.BbvC IA, N.BbvC IB, or the like, such that after the dsDNA is nicked, it is amplified by rolling circle amplification using a DNA polymerase having strand displacement activity, such as φ29 DNA polymerase, or the like (e.g. disclosed in Mahtani, U.S. Pat. No.6,221,603, which is incorporated herein by reference). In another alternative, the dsDNA circles can be linearized and amplified by PCR.

An exemplary embodiment of the method of the invention is illustrated in FIGS. 1A-1D. To each of a plurality of target polynucleotides (100) is annealed selection primer (103) that has a 3' end (110) that forms an extendable duplex with a predetermined segment of target polynucleotide (100). Selection primer (103) further comprises in its non-complementary region, a 5' end (102) that has a sequence complementary to a 5' end of a connector oligonucleotide and a 5' terminal phosphate group to permit ligations, discussed further below. In the illustrated embodiment, the non-complementary region of selection primer (103) also contains restriction endonuclease site (106) sandwiched between primer binding sites (104) and (108). The length of the eventual amplicon produced in the method of the invention is determined by the selection of region (112) on the target polynucleotide. As explain more fully below, dsDNA circles are formed by the hybridization of connector oligonucleotide to the 5' ends and regions complementary to region (112) of the extended selection primers. Thus, segment (101) of target polynucleotide (100) that extends from 3' end (110) to region (112) is amplified in the method of the invention. After annealing of selection primers (103) to their respective target polynucleotides using conventional protocols, 3' ends (110) are extended (114) with nucleic acid polymerase (116), again using conventional protocols. As mentioned above, preferably, nucleic acid polymerase (116) forms the complement of the template strand, that is the target polynucleotide, with high fidelity. A result of the extension by nucleic acid polymerase is the formation of extended selection primer (119) that includes segment (118) that is the complement of region (112). Extended selection primers (119) are then melted from target polynucleotide strands (100), combined with connector oligonucleotides (124), and re-annealed (120) under-conditions favoring the formation of complexes (125) between connector oligonucleotides (124) and extended selection primers (119). As illustrated, such complexes arise by the formation of stable duplexes both between region (118) of extended selection primers (119) and region (122) at 3' ends of connector oligonucleotides (124) and between region (102) at 5' ends of extended selection primers (119) and region (126) at 5' ends of connector oligonucleotide (124). In one aspect, such complexes usually have a 3' "tail" (127) of extended selection primers (119) that extends beyond the duplex formed between regions (118) and (122). To such complexes are added (130) a DNA polymerase (134) and DNA ligase (132) under conditions that permit the enzymes to act on the complexes. In one aspect, such enzymes are added simultaneously. Preferably, DNA polymerase has strong 3'→5' single stranded exonuclease activity and substantially no strand displacement activity, such as T4 DNA polymerase or T7 DNA polymerase. A variety of DNA ligase can be used, such as Taq DNA ligase or E. coli DNA ligase. DNA polymerase (134) both extends (136) 3' end of connector oligonucleotide (124) and digests (138) the 3' tail of extended selection primers (119). After such 3' tails are digested to duplexes (133), the DNA polymerase starts extending (140) region (118) using connector oligonucleotide (124) as a template. After the extended sequences reach the 5' ends (148) and (150) of the extended selection primer and connector oligonucleotide, respectively, eventually polymerases (134) dissociate (144) from the complex and are replaced (146) by ligases (132), where upon the sequences are ligated to form dsDNA circle (151). After optionally digesting noncircularized nucleic acids using one or more single stranded exonucleases, dsDNA circle (151) is linearized by treating with the endonuclease corresponding to restriction site (106) disposed between primer binding sites (104) and (108). After linearization, the sequences (155) are amplified using common primers (154) and (156).

FIGS. 2A-2D illustrate an alternative embodiment wherein one primer binding site is in the selection primer and the other primer binding site is in the connector oligonucleotide, thereby reducing the length of the selection primer. Selection primer (203) comprises target-binding region (210), first primer region (206), restriction site (204), and 5' end (202). After annealing to target polynucleotide (200), target-binding region (210) is extended by DNA polymerase (216) over region (201) and region (212) of target polynucleotide (200) to produce (215) extended selection primer (217). After melting extended selection primer (217) from target polynucleotide (200), connector oligonucleotide (223) is added under conditions that permit it to form complex (229) with its associated extended selection primer (217). As with the embodiment of FIG. 1, 3' end (222) of connector oligonucleotide (223) forms a duplex with region (218) of extended selection primer (217) and 5' end (228) of connector oligonucleotide (223) forms a duplex with 5' end (202) of extended selection primer (217). Connector oligonucleotide (223) further comprises second primer binding site (224) and second restriction site (226). Optionally, either connector oligonucleotide (223) or extended selection primer (217), or both, can additionally comprise oligonucleotide tags or barcodes sequences. To such complexes is added a DNA polymerase and a ligase so that a dsDNA circle is formed substantially as described above. dsDNA circle (243) can be linearized by digesting it with first and second restriction endonucleases (which may be the same) that recognize first and second restriction sites (204) and (226) to give fragments (258) and (260). Fragment (258) is amplified by common primers (254) and (256).

Figure 3A:
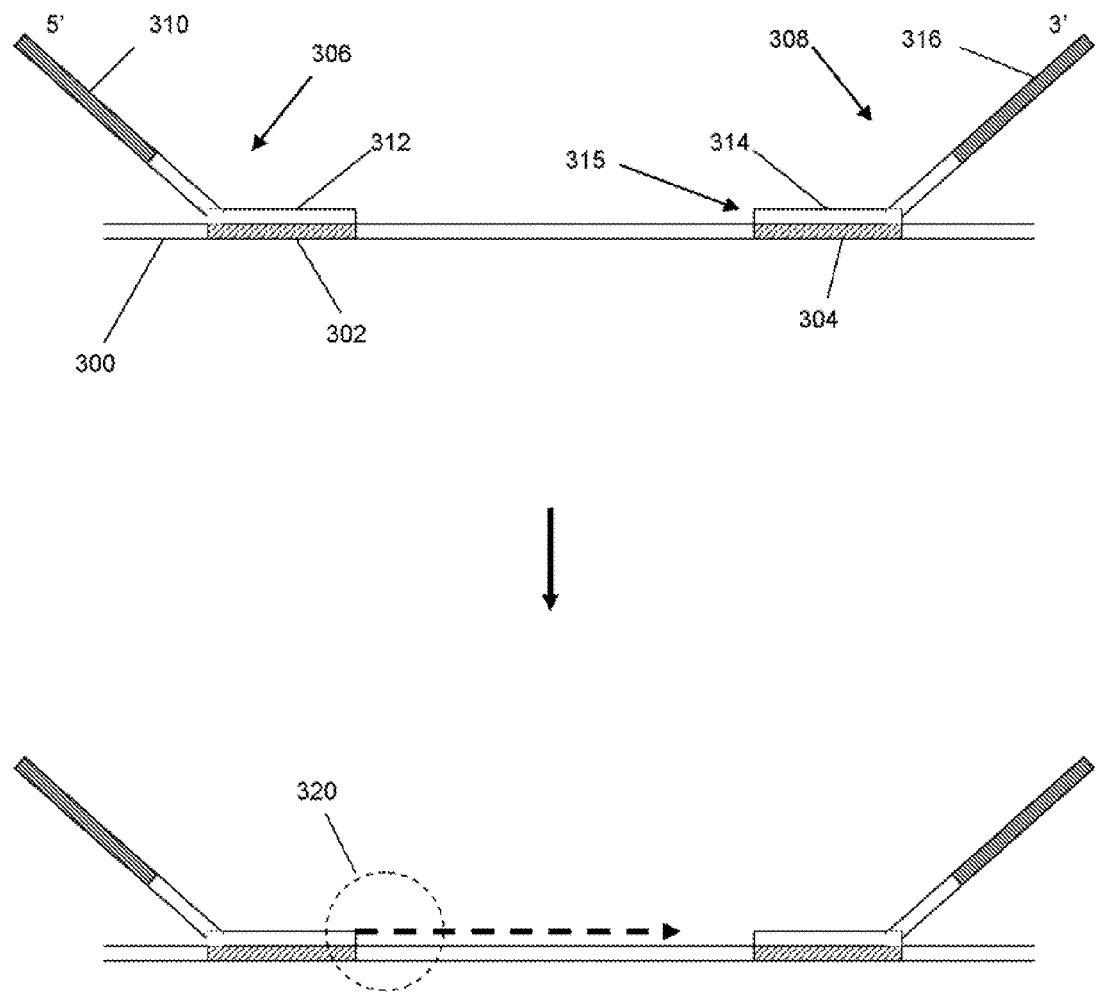
FIGS. 3A-3C illustrate steps of an embodiment wherein two selection primers and one connector oligonucleotide are employed for each target polynucleotide.
Figure 3B:
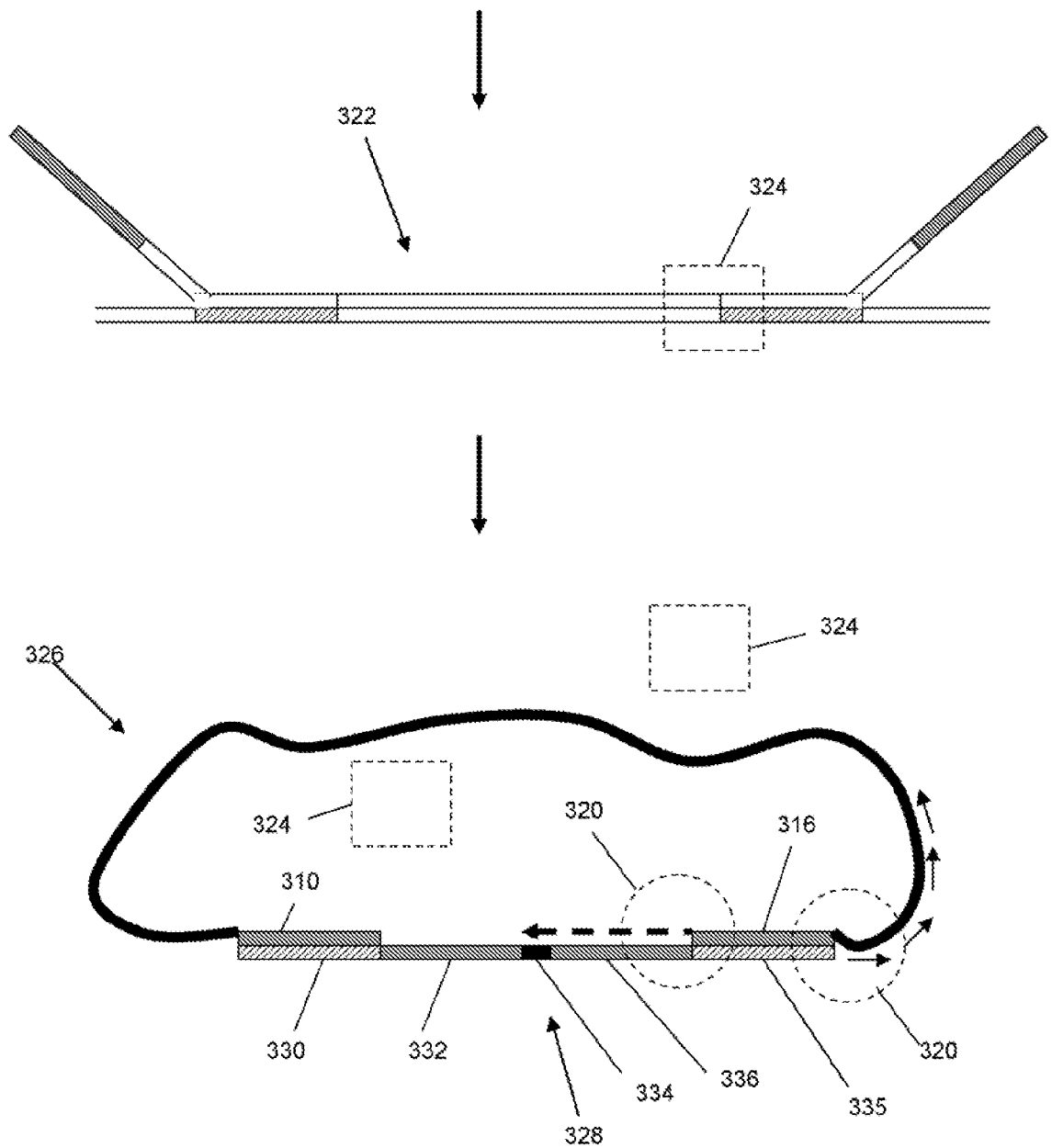
Figure 3C:
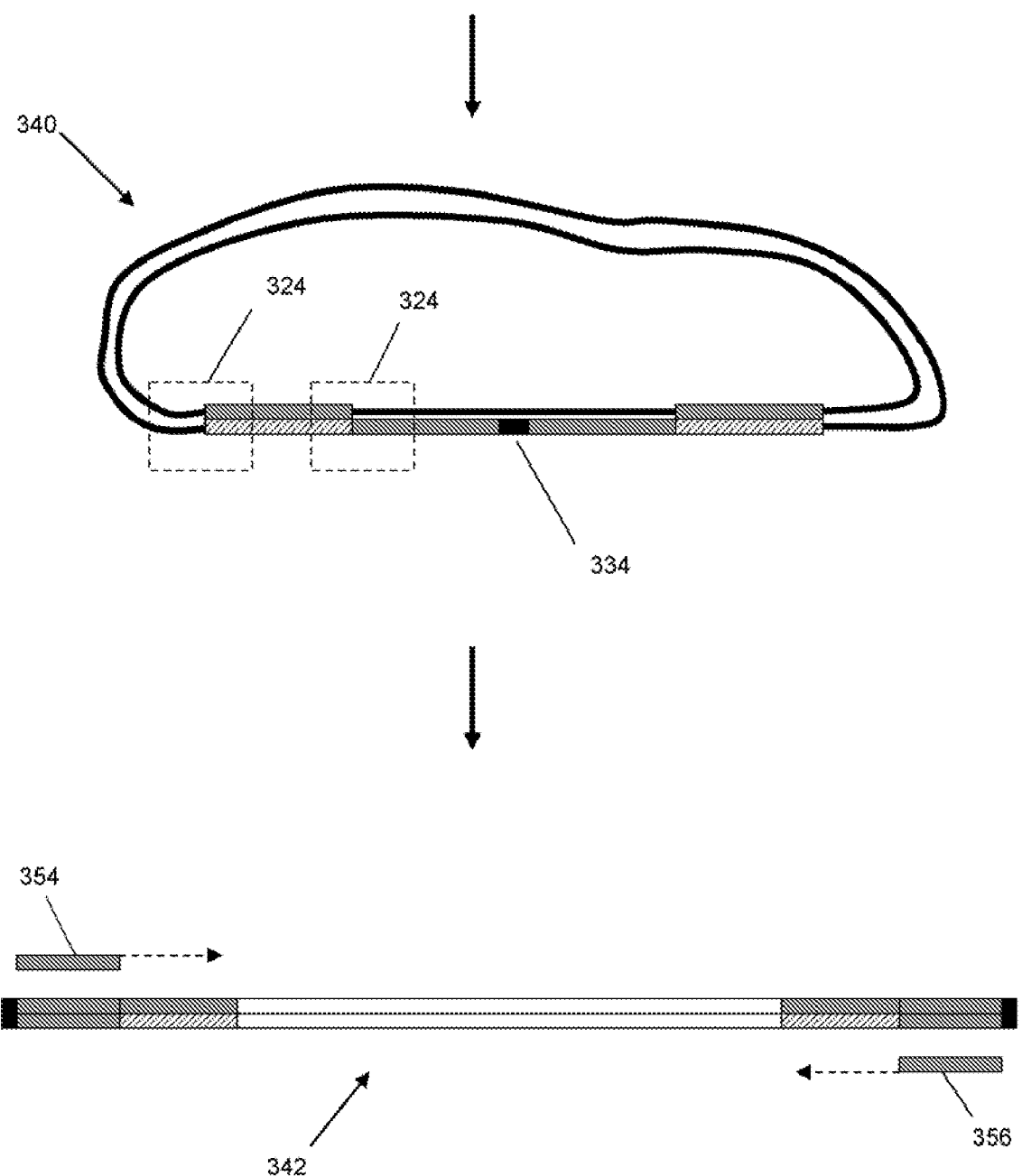

FIGS. 3A-3C illustrate an embodiment of the invention in which two selection primers are employed to generate an extended selection primer. First sequence region (312) and second sequence region (314) of first selection primer (306) and second selection primer (308), respectively, are annealed to first and second predetermined sequence regions (302) and (304), respectively, of target polynucleotide (300). First selection primer (306) has 5' end (310) with a sequence complementary with an end of an associated connector oligonucleotide. In one aspect, sequence of 5' end (310) is unique to first selection primer (306) and target polynucleotide (300). Second selection primer (308) has 3' end (316) with a sequence complementary with the opposite end of the associated connector oligonucleotide. As with the sequence of 5' end (310), in one embodiment, the sequence of 3' end (316) is unique to second selection primer (308) and target polynucleotide (300). Second selection primer (308) further has a phosphate group at its 5' end (315) to permit ligation to adjacent oligonucleotides. To the annealed first and second selection primes (306) and (308), a nucleic acid polymerase (320) is added for extending first selection primer (306) using target polynucleotide (300) as a template. In this embodiment, extension is halted when second primer (308) is reached, after which the extended end of first selection primer (306) is ligated with ligase (324) to 5' end (314) of second selection primer (308) to from extended selection primer (322). After melting extended selection primer (322) from target polynucleotide (300), it is combined with connector oligonucleotide (328) to form complex (326). Connector oligonucleotide (328) comprises phosphorylated 5' end (330) that forms a duplex with 5' end (310) of first selection primer (306), primer binding sites (332) and (336) and (optionally) restriction site (334) disposed therebetween, and 3' end (335) that form a duplex with 3' end (316) of second selection primer (308). After formation of complex (326), 3' end (316) and 3' end (335) are extended with DNA polymerase (320) in a reaction that may also contains ligase (324). Preferably, DNA polymerase (320) has substantially no strand displacement activity. After 3' end (335) has been extended to 5' end (330) and 3' end (316) has been extended to 5' end (310), the resulting nicks are ligated by ligase (324) to form closed double stranded DNA circle (340). In a preferred embodiment, dsDNA circle (340) is linearized by cleaving it at restriction site (334), after which linear double stranded sequence (342) is amplified in a PCR using primers (354) and (356).

Figure 4A:
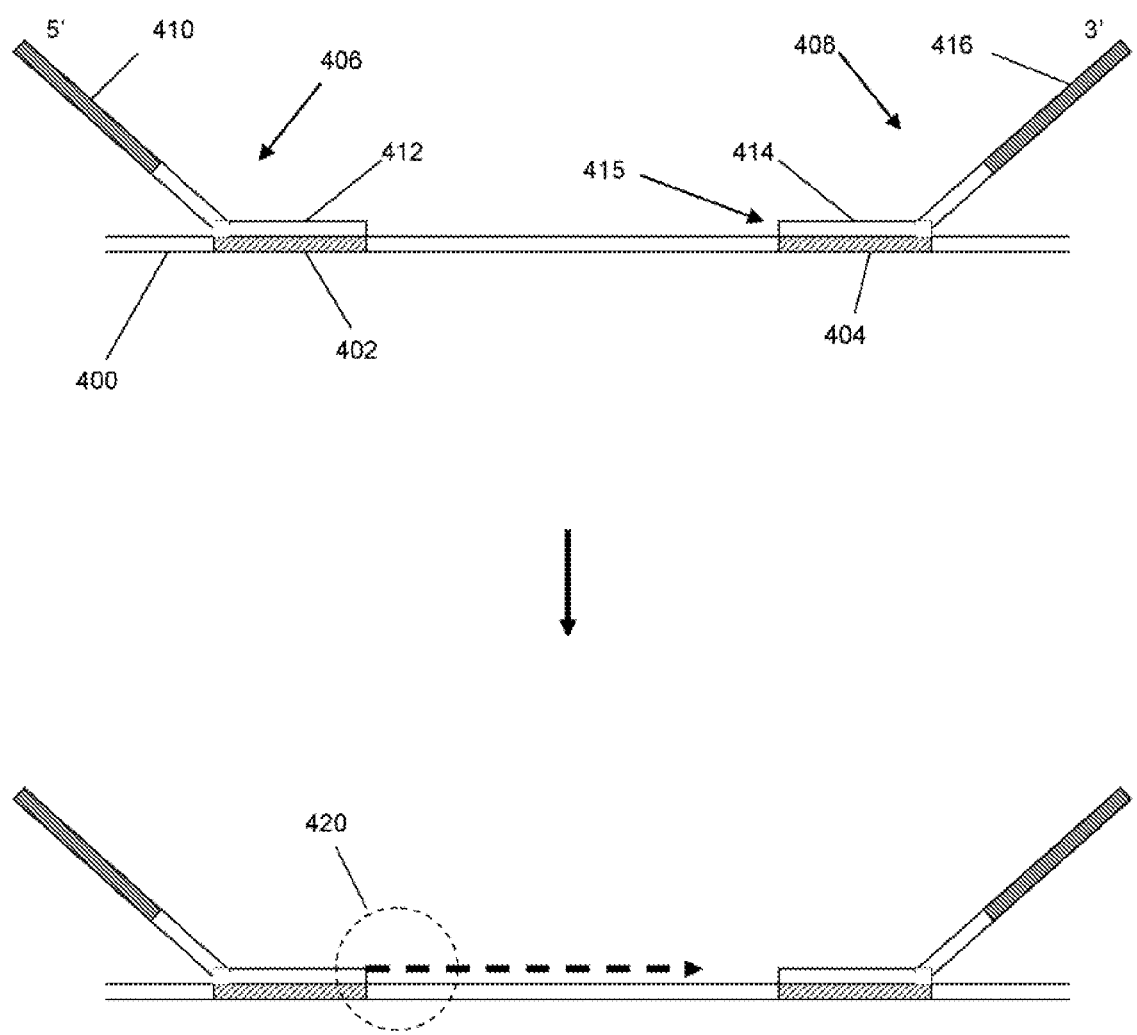
FIGS. 4A-4B illustrate steps of an embodiment wherein pairs of selection primers are employed without connector oligonucleotides for amplifying target polynucleotides.
Figure 4B:
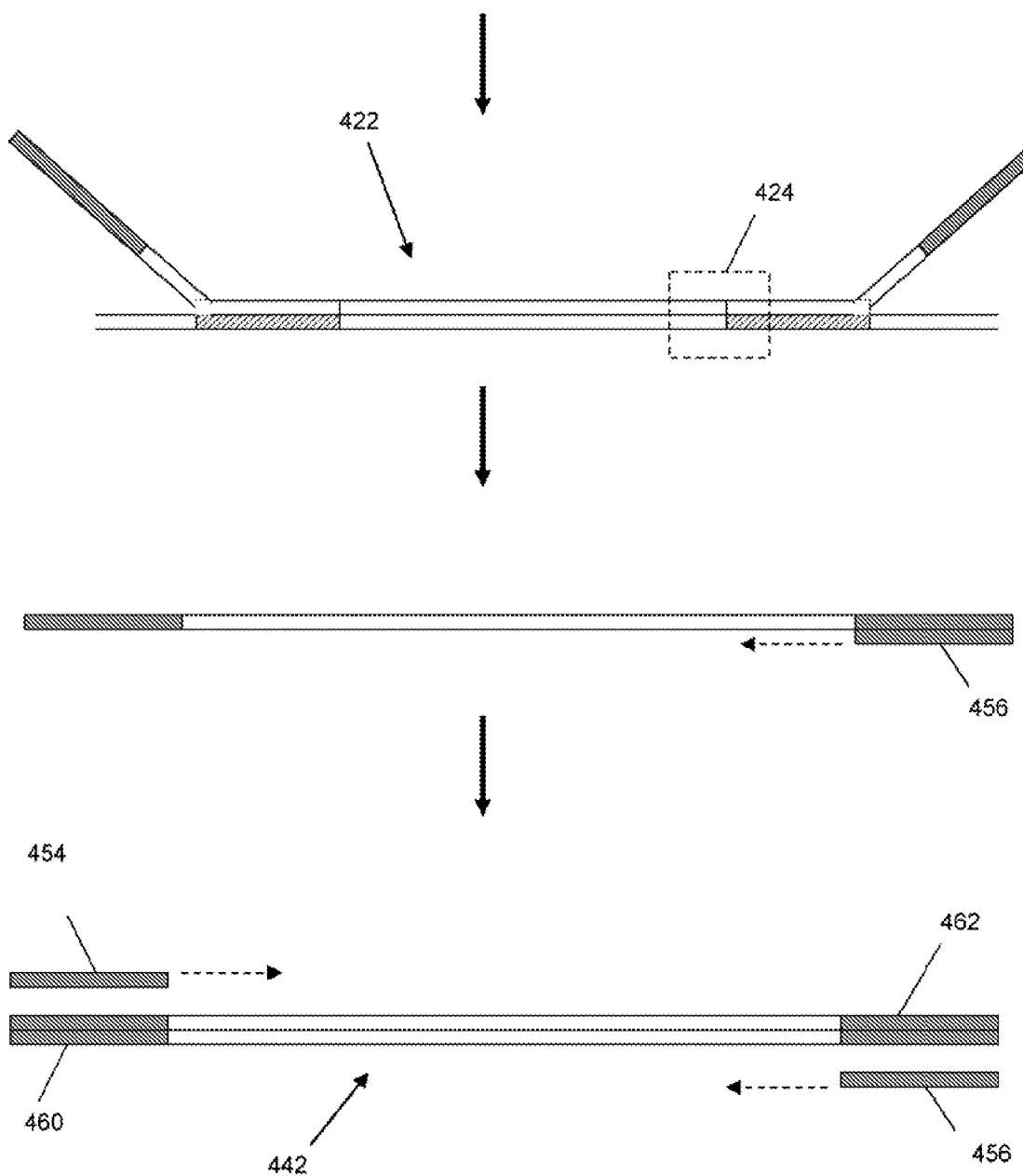

FIGS. 4A-4B illustrate an embodiment of the invention in which two selection primers are employed to generate an extended selection primer and no connector oligonucleotide is employed to form a closed ds DNA circle. First sequence region (412) and second sequence region (414) of first selection primer (406) and second selection primer (408), respectively, are annealed to first and second predetermined sequence regions (402) and (404), respectively, of target polynucleotide (400). First selection primer (406) has 5' end (410) with a sequence complementary with an end of an associated connector oligonucleotide. In one aspect, sequence of 5' end (410) is unique to first selection primer (406) and target polynucleotide (400). Second selection primer (408) has 3' end (416) with a sequence complementary with the opposite end of the associated connector oligonucleotide. As with the sequence of 5' end (410), in one embodiment, the sequence of 3' end (416) is unique to second selection primer (408) and target polynucleotide (400). Second selection primer (408) further has a phosphate group at its 5' end (415) to permit ligation to adjacent oligonucleotides. To the annealed first and second selection primers (406) and (408), a nucleic acid polymerase (420) is added for extending first selection primer (406) using target polynucleotide (400) as a template. In this embodiment, extension is halted when second selection primer (408) is reached, after which the extended end of first selection primer (406) is ligated with ligase (424) to 5' end (414) of second selection primer (408) to from extended selection primer (422). Preferably, nucleic acid polymerase (420) is a DNA polymerase lacking strand displacement activity, such as T4 DNA polymerase. For DNA polymerases, such as T4 DNA polymerase, that have 3'→5' exonuclease activity, 3' end (416) of second selection primer (408) can be produced with nuclease resistant linkages, such as phosphorothioate linkages. After melting extended selection primer (422) from target polynucleotide (400), it is combined with primer (456) to form double stranded sequence (442), after which it is amplified in a PCR, or like amplification technique, using primers (454) and (456) that are specific for primer binding sites (460)(complementary to a region of 5' end (410)) and (462)(having a sequence identical to a region of 3' end (416)). respectively. Sequences of and adjacent to) 5' end (410) and 3' end (416) can be selected to add in the detection or manipulation of the amplified target polynucleotide, e.g. restriction sites, oligonucleotide tag sequences, and, the like, can be inserted.

Figure 5:
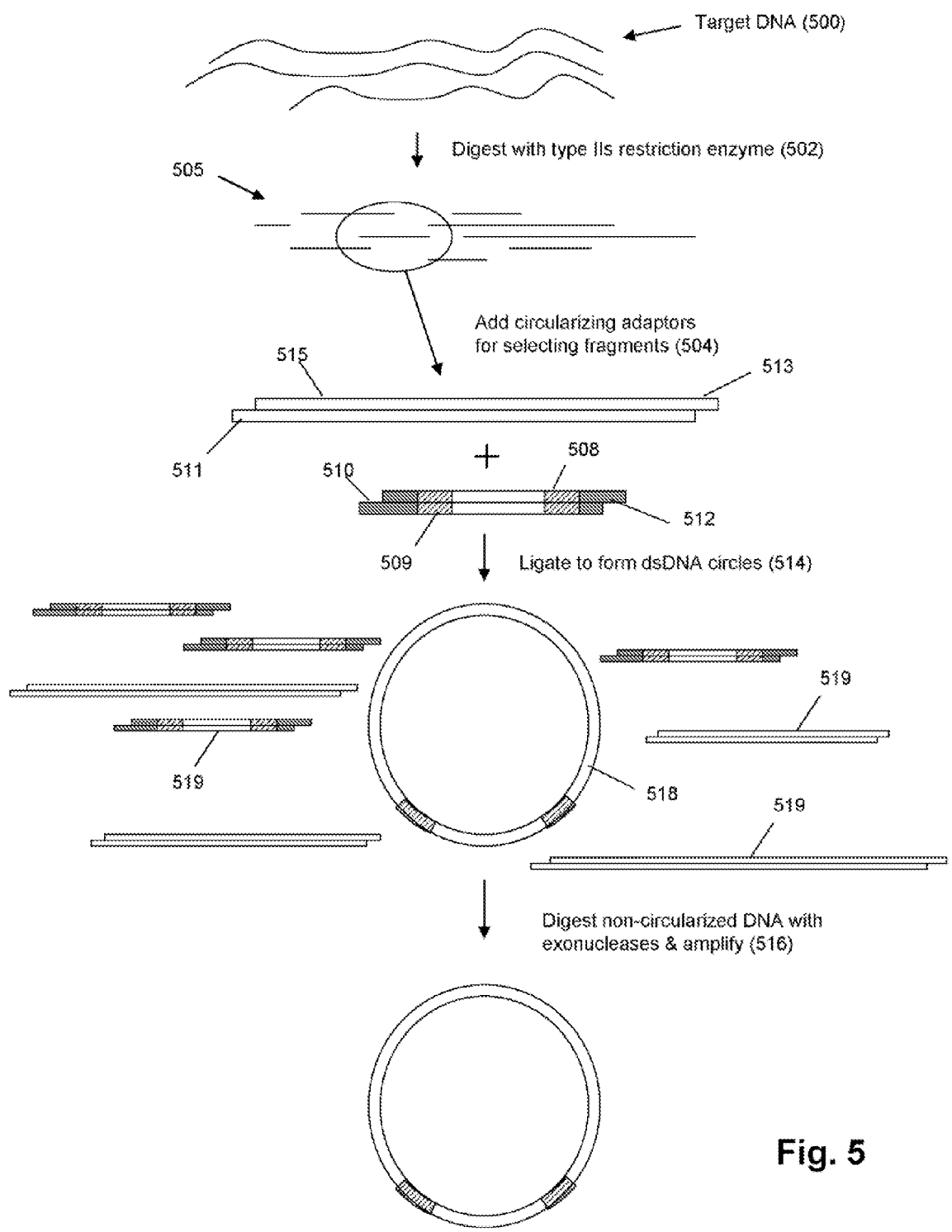
FIG. 5 illustrates steps of an embodiment wherein circularizing adaptors are using to selected fragment after digestion of target DNA with restriction enzymes having interrupted recognition sites.

Another aspect of the invention is illustrated in FIG. 5 where sequences are selected for amplification using one or more restriction endonucleases that have cleavage sites separate from their recognition sites (referred to herein as "type IIs" restriction endonucleases). Digestion with such enzymes produces fragments having overhangs with random nucleotides (referred to herein as "random-end fragments"). In this aspect, the method takes advantage of prior knowledge of the nucleotide sequence(s) of target polynucleotides in the following manner. First, the recognition sequences of the restriction endonucleases define a set of random-end fragments, and second the sequences of the random ends permit individual fragments to be selected. For a given sized genome, selecting appropriate type IIs restriction endonucleases is a matter of routine design choice. An important factor in such selection is to ensure that the random ends produced by the selected type IIs enzymes provide enough diversity to permit individual fragments to be identified. For example for the human genome ($\approx 3 \times 10^9$ basepairs), Bac I (5–(10/15)ACNNNNG-TAYC(12/7)) generates (on average) about $3.6 \times 10^5$ fragments each having an average length of eight kilobases and each having two 5-nucleotide random sequence overhangs. Ten nucleotides of random sequences provides more than enough diversity ($4^{10} \approx 1.05 \times 10^6$ sequences) so that individual fragments can be selected by providing a circularizing adaptor with complementary ends. Exemplary type IIs restriction endonuclease that can be used with this aspect of the invention include, but are not limited to, Bae I, Alo I, Ppi I, Psr I, Bpl I, Fal I, Hae IV, Bbv I, Aar I, Bbr 7 I, Bsa XI, Bsl F1, Bsm B1, Bsp M1, Btg ZI, Cje I, Cje PI, Ear I, Fok I, Hin4 I, Sts I, and the like. Returning to FIG. 5, target DNA (500) is digested (502) with one or more type IIs restriction endonucleases to produce a population of random-end fragments (505), after which the restriction endonucleases are disabled, e.g. by heating. Circularizing adaptor (507) having ends (510) and (512) complementary to ends (511) and (513) of fragment (515) to be selected is added to fragments (505) under conditions that permit the fragment (515) and circularizing adaptor (507) to be ligated (514) to form dsDNA circles (518). Circularizing adaptor (507) preferably contains elements, such as primer sites (508) and (509), restrictions site, and the like, that permit selected dsDNA circles (518) to be amplified and otherwise manipulated and labeled. Preferably, polynucleotides and fragments that do not circularize (519) are destroyed by digesting (516) them with one or more exonucleases, thereby removing a possible source of background signal. Finally, the dsDNA circles remain can be amplified by any of several available techniques for further analysis of the selected fragments.

Figure 6A:
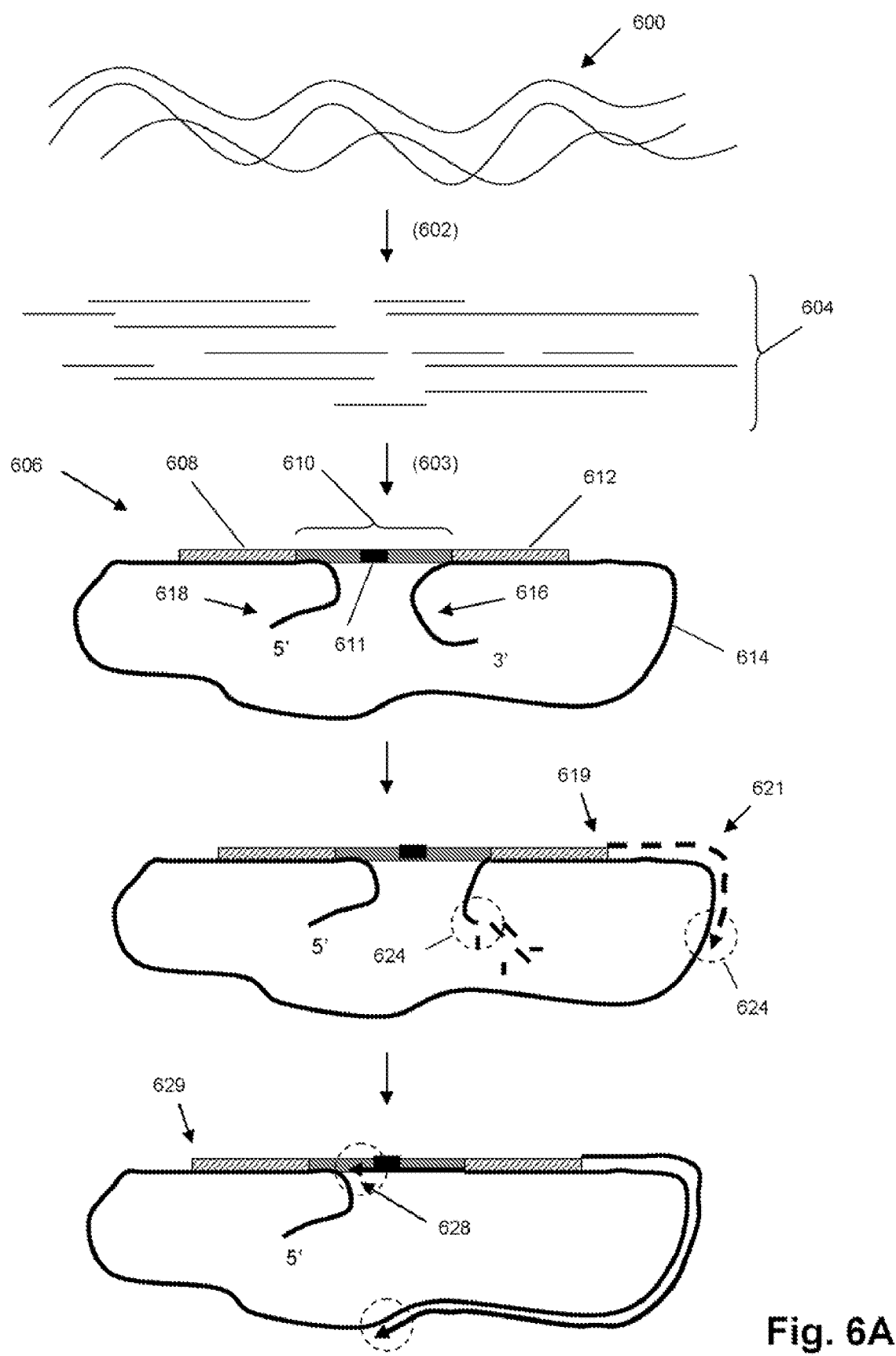
FIGS. 6A-6B illustrate steps of an embodiment for forming double stranded DNA circles using a single selection oligonucleotide and randomly sheared DNA, and the optional amplification of the selected sequences.
Figure 6B:
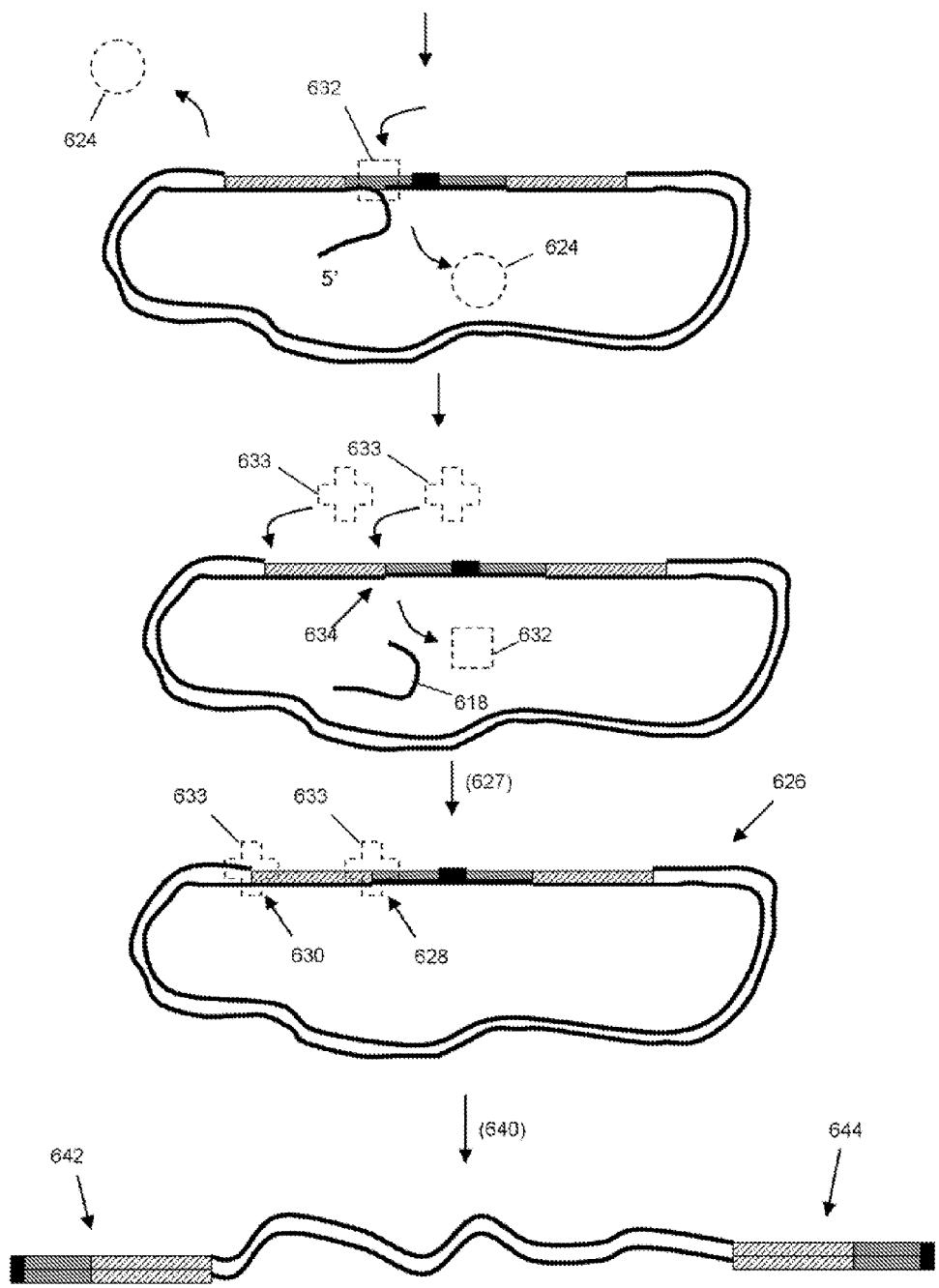

FIGS. 6A-6B illustrate another embodiment of the invention wherein a target polynucleotide is selected by a selection oligonucleotide and converted into a closed double stranded DNA circle that optionally may be amplified. DNA (600) from a sample is fragmented and denatured (602) to form single stranded target polynucleotides (604). Fragmentation may be accomplished using conventional chemical, enzymatic, or mechanical fragmentation protocol. In one aspect, random fragments are produced. To fragments (604) selection oligonucleotide is added so that a 5' target-specific segment (608) and a 3' target-specific segment (612) anneal to target polynucleotide (614) and so that the 5' end selection oligonucleotide (606) is phosphorylated and the 3' end of selection oligonucleotide (606) is extendable along target polynucleotide (614). In the case where fragmentation is random, the complex between selection oligonucleotide (606) and target polynucleotide (614) showing free 5' strand (618) and free 3' strand (616) may represent only a fraction of possible complexes, as some target polynucleotides may have only a single complementary region to the 3' of 5' target-specific segments of the selection oligonucleotide, or one or both of the 3' and 5' free strands may be lacking. However, a subset shall be present for which the indicated configuration is representative. Selection oligonucleotides (606) optionally have internal segment (610) containing restriction site (611) that, as shown later, may be used to linearize the dsDNA circle for PCR amplification. Fragments (604) and selection oligonucleotides (606) are combined in a reaction mixture comprising the following enzymatic activities: (i) a 5' flap endonuclease activity, (ii) a DNA polymerase lacking strand displacement activity, (iii) a 3' single stranded exonuclease activity, and (iv) a ligase activity. In a preferred embodiment, such activities are provided by a FEN 1 nuclease, a T4 DNA polymerase, and a ligase, such as a T4 ligase. Such enzymes are disclosed in the following references that provide guidances for their use: Lieber, BioEssays, 19:233-240 (1997); Kaiser et al, J. Biol. Chem. 274:21387-21394 (1999); and U.S. Pat. Nos. 7,122,364; 6,562,611; and 6,555,257; which reference are incorporated herein by reference. In the reaction mixture, which includes nucleoside triphophates and other appropriate salts and/or cofactors. DNA polymerase (624) extends (621) 3' end (619) of selection oligonucleotide (606) and, whenever T4 DNA polymerase is employed, digests (622) free 3' strand (616). After digestion of free 3' strand (616) to the portion anneal to selection oligonucleotide (606), the same strand is extended along selection oligonucleotide (606) to form an extension product that abuts (628) free 5' strand (618). Likewise, 3' end (619) of selection oligonucleotide (606) is extended to form an extension product that abuts 5' end (629) of selection oligonucleotide (606) to form first nick (630). Through normal exchange between the enzymes and their substrates, polymerase (624) exchanges with 5' flap endonuclease (632), which cleaves 5' free strand (618) to leave second nick (634). Both first and second nicks (630 and 628) are ligated by ligase (633) to form (627) closed double stranded DNA circle (626), which may be cleaved (640) at restriction site (611) to form a linear double strand DNA that may be amplified by PCR using primers specific for regions (642) and (644).

In one aspect, the number of target polynucleotides amplified by a method of the invention depends on numerous factors known to those of ordinary skill in the art including, but not limited to, the type of nucleic acid e.g. RNA or DNA, that makes up the target polynucleotides, the quality of the sample, e.g. if and to what degree the target polynucleotides of the sample are degraded, the differences among the selection primer binding sites, the presence or absence of potentially interfering or homologous sequences in the sample, and the like. In one aspect, the number of target polynucleotides amplified in a method of the invention is in the range of from 10 to 1000; and in another aspect, such number is in the range of from 10 to 500; and in another aspect, such number is in the range of from 10 to 100, and in another aspect, such number is in the range of from 10 to 50.

The concentrations of connector oligonucleotides and/or selection oligonucleotides is a matter of design choice for those of ordinary skill in the art; however, in one aspect, such concentrations may be selected that are equivalent to those used in conventional amplification reactions, such as PCR reactions. Generally, such concentrations are selected following well-known principles of hybridization reactions and PCR primer selections for example, disclosed in the references cited below.

DEFINITIONS

Terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992) Lehninger, Biochemistry, Second Edition (Worth Publishers, New York, 1975); Strachan and Read, Human Molecular Genetics, Second Edition (Wiley-Liss, New York, 1990); Eckstein editor, Oligonucleotides and Analogs: A Practical Approach (Oxford University Press, New York, 1991); (Gait, editor, Oligonucleotide Synthesis: A Practical Approach (IRL Press, Oxford, 1984); and the like.

"Addressable" or "addressed" in reference to tag complements means that the nucleotide sequence, or perhaps other physical or chemical characteristics of a tag complement can be determined from its address, i.e. a one-to-one correspondence between the sequence or other property of the tag complement and a spatial location on, or characteristic of, the solid phase support to which it is attached. Preferably, an address of a tag complement is a spatial location, e.g. the planar coordinates of a particular region containing copies of the tag complement. However, tag complements may be addressed in other ways too, e.g. by microparticle size, shape, color, signal of micro-transponder, or the like, e.g. Chandler et al, PCT publication WO 97/14028.

"Allele frequency" in reference to a genetic locus, a sequence marker, or the site of a nucleotide means the frequency of occurrence of a sequence or nucleotide at such genetic loci or the frequency of occurrence of such sequence marker, with respect to a population of individuals. In some contexts, an allele frequency may also refer to the frequency of sequences not identical to, or exactly complementary to, a reference sequence.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in the base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683, 195; 4,965,188, 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japenese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26:2150-2155 (1998), and like reference. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least 65% complementary over a stretch of at least 14 to 25 nucleotides, preferably at least about 75%, more preferable at least about 90% complementary. See, M. Kanehisa Nucleic Acids Res. 12:203 (1984), incorporated herein by reference.

"Complexity" or "complex" in reference to mixtures of nucleic acids means the total length of unique sequences in the mixture. In reference to genomic DNA, complexity means the total length of unique sequence DNA in a genome. The complexity of a genome can be equivalent to or less than the length of a single copy of the genome (i.e. the haploid sequence). Estimates of genome complexity can be less than the total length if adjusted for the presence of repeated sequences. In other words, in reference to genomic DNA, "complexity" means the total number of basepairs present in non-repeating sequences, e.g. Wetmur, Critical Reviews in Biochemistry and Molecular Biology, 26:227-259 (1991); Britten and Davidson, chapter 1 in Hames et al, editors, Nucleic Acid Hybridization: A Practical Approach (IRL Press, Oxford, (1985).

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g. conditions including temperature of about 5° C. less that the $T_m$ of a strand of the duplex and low monovalent salt concentration, e.g. less than 0.2 M, or less than 0.1 M. "Perfectly matched" in reference to a duplex means that the poly- or oligonucleotide strands making up the duplex from a double Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that at pair of nucleotides in the duplex fails to undergo Watson-Crick bonding.

"Fragment", "segment", or "DNA segment" refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical Fragmentation methods may likewise be employed such as fragmentation by heat an ion-mediated hydrolysis. See for example, Sambrook et al., "Molecular Cloning: A Laboratory Manual," $3^{rd}$ Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range. Where the nucleic acid sample contains RNA, the RNA may be total RNA, poly(A)+ RNA, mRNA, rRNA, or tRNA, and may be isolated according to methods known in the art. See, e.g., Sambrook and Russel, *Molecular Cloning: A Laboratory Manual.* (Cold Spring Harbor Lab, Cold Spring Harbor, N.Y. 2001). The RNA may be heterogeneous, referring to any mixture of two or more distinct species of RNA. The species may be distinct based on any chemical or biological differences, including differences in base composition, length, or conformation. The RNA may contain full length mRNAs or mRNA fragments (i.e., less than full length) resulting from in vivo, in situ, or in vitro transcriptional events involving corresponding genes, gene fragments, or other DNA templates. In a preferred embodiment, the mRNA population of the present invention may contain single-stranded poly(A)+ RNA, which may be obtained from a RNA mixture (e.g., a whole cell RNA preparation), for example, by affinity chromatography purification through an oligo-dT cellulose column.

"Genetic locus," or "locus" in reference to a genome or target polynucleotide, means a contiguous subregion or segment of the genomic or target polynucleotide. As used herein, genetic locus or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions.

"Hybridization" refer to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM less than about 200 mM. Hybridization temperatures can be as low as 5° C. but are typically greater than 22° C. more typically greater than about 30° C., and preferably in excess of about 37° C., Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 5.0 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A Laboratory Manual" $2^{nd}$ Ed. Cold Spring Harbor Press (1989) and Anderson "Nucleic Acid Hybridization" $1^{st}$ Ed. BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Hybridization-based assay" means any assay that relies on the formation of a stable duplex or triplex between a probe and a target nucleotide sequence for detecting or measuring such a sequence. In one aspect, probes of such assays anneal to (or form duplexes with) regions of target sequences in the range of from 8 to 100 nucleotides; or in other aspects, the anneal to target sequences in the range of from 8 to 40 nucleotides, or more usually, in the range of from 8 to 20 nucleotides. A "probe" in reference to a hybridization-based assay mean a polynucleotide that has a sequence that is capable of forming a stable hybrid (or triplex) with its complement in a target nucleic acid and that is capable of being detected, either directly or indirectly. Hybridization-based assays include, without limitation, assays based on use of oligonucleotide, such as polymerase chain reactions, NASBA reactions, oligonucleotide ligation reactions, single-based extensions of primers, circularizable probe reactions, allele-specific oligonucleotides hybridizations, either in solution phase in solution phase or bound to solid phase supports, such as microarrays or microbeads. There is extensive guidance in the literature on hybridization-based assays, e.g. Hames et al, editors, Nucleic Acid Hybridization a Practical Approach (IRL Press, Oxford, 1985), Tijssen, Hybridization with Nucleic Acid Probes, Parts I & II (Elsevier Publishing Company, 1993); Hardiman, Microarray Methods Applications (DNA Press, 2003); Schena, editor, DNA Microarrays a Practical Approach (IRL Press, Oxford, 1990); and the like. In one aspect, hybridization-based assays are solution phase assays; that is, both probes and target sequences hybridize under conditions that are substantially free of surface effects influences on reaction rate. A solution phase assay may include circumstances where either probes or target sequences are attached to microbeads.

"Kit" refers to any delivery system for delivering materials or reagents for carrying out a method of the invention. In the context of assays, such delivery systems include systems that allow for the storage, transport, or delivery of reaction reagents (e.g. probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting material for assays of the invention. In one aspect, kits of the invention comprises one or more pluralities probes each plurality of probes being specific for a different target polynucleotide such as a genetic locus, a gene expression product, or the like. In another aspect, such probes comprise circularizable padlock probes. Such contents may be delivered to the intended recipient together or separately. For example, a first container may contain an enzyme for use in an assay, while a second container contains probes.

"Ligation" means to form a convalent bond or linkage between the termini of two or more nucleic acids, e.g. oligonucleotide and/or polynucleotide, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4.883, 750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27:875-881 (1999); Higgins et al, Methods in Enzymology, 68:50-71 (1979); Engler et al. The Enzymes. 15:3-29 (1982); and Namsaraev, U.S. patent publication 2004/0110213.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known, predetermined, or determinable. Typically, the oligonucleotides or polynucleotides are single stranded and are covalently attached to thee solid phase support usually by a 5'-end or a 3'-end. The density of non-overlapping regions containing nucleic acids in a microarray is typically greater than 100 per $cm^2$, and more preferably, greater than 1000 per $cm^2$.

Microarray technology is reviewed in the following references. Schena, Editor, Microarray. A Practical Approach (IRL Press, Oxford, 2000); Southern, Current Opin. Chem. Biol., 2:404-410 (1998); Nature Genetics Supplement, 21:1-60 (1999). As used herein, "random microarray" refers to a microarray whose spatially discrete regions of oligonucleotides or polynucleotides are not spatially addressed, absent a decoding step to identify the sequence of an immobilized oligonucleotide. That is, the identity of the attached oligonucleotides or polynucleotides is not discernable, at least initially, from its location; it requires a decoding step to determine which probe or tag hybridizes to which site. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology 18:630-634 (2000); Tulley, et al, U.S. Pat. No. 6,133,043; Stuelpnagel et al, U.S. Pat. No. 6,396,995; Chee et al, U.S. Pat. Nos. 6,544,732; 6,620,584; and the like. Likewise, microbeads solid supports e.g. in a random array, may be identified, or addressable, in a variety of ways, including by optical labels, e.g. fluorescent dye ratios or quantum dots, shape, sequence analysis, radio frequency identification tags, or the like.

"mRNA or mRNA transcripts" include, by not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, a cRNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA. DNA amplified from the genes, RNA transcribed from amplified DNA, and the like.

"Nucleoside" as used herein includes the natural nucleosides, including 2'-deoxy and 2'-hydroxyl forms, e.g. as described in Komberg and Baker. DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980): Uhlman and Peyman, Chemical Reviews, 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above): Crooke et al, Exp. Opin. Ther. U.S. Pat. No. 6:855,870 (1996), Mesmacker et al, Current Opinion in Structured Biology, 5:343-355 (1995); and the like. Exemplary types of polynucleotides that are capable of enhancing duplex stability include oligonucleotide N3'+→P5' phosphoramidates (referred to herein as "amidates"), peptide nucleic acids (referred to herein as "PNAs"), oligo-2'-O-alkylribonucleotides, polynucleotides containing C-5 propynlpyrimidines, locked nucleic acids (LNAs), an like compounds.

Such oligonucleotides are either available commercially or may be Synthesized using methods described in the literature.

"Oligonucleotide tag" means an oligonucleotide that is attached to a polynucleotide and is used to identify and/or track the polynucleotide in a reaction. Usually, a oligonucleotide tag is attached to the 3'- or 5'-end of a polynucleotide to form a linear conjugate, sometime referred to herein as a "tagged polynucleotide," or equivalently, a "oligonucleotide tag-polynucleotide conjugate," or "tag-polynucleotide conjugate." Oligonucleotide tags may vary widely in size and compositions; the following references provide guidance for selecting sets of oligonucleotide tags appropriate for particular embodiments: Brenner, U.S. Pat. No. 5,635,400; Brenner et al, Proc. Natl. Acad. Sci. 97:1665-1670 (2000), Shoemaker et al, Nature Genetics, 14:450-456 (1996); Morris et al, European patent publication 0799897A1; Wallace, U.S. Pat. No. 5,981,179; and the like. In different applications of the invention, oligonucleotide tags can each have a length within a range of from 4 to 36 nucleotides, or from 6 to 30 nucleotides, or from 8 to 20 nucleotides, respectively. In one aspect, oligonucleotide tags are used in sets, or repertoires, wherein each oligonucleotide tag of the set has a unique nucleotide sequence. In some embodiment, particularly where oligonucleotide tags are used to sort polynucleotides, or where they are identified by specific hybridization, each oligonucleotide tag of such a set has a melting temperature that is substantially the same as that of every other member of the same set. In such aspects, the melting temperatures of oligonucleotide tags within a set are within 10° C. of one another, in another embodiment, they are within 5° C. of one another; and in another embodiment, they are within 2° C. of one another. In another aspect, oligonucleotide tags are members of a mutually discriminable set as described more fully below. The size of mutually discriminable sets of oligonucleotide tags may vary widely. Such a set of oligonucleotide tags may have a size in the range of from several tens to many thousands, or even millions, e.g. 50 to $1.6 \times 10^6$. In another embodiment, such a size is in the range of from 200 to 40,000; or from 1000 to 40,000; or from 1000 to 10,000. In another aspect of the invention of oligonucleotide tags comprise a concatenation of subunits, such as described by Brenner et al, Proc. Natl. Acad. Sci., 97:1665-1670 (2000). In such concatenates, oligonucleotide subunits, or words, can be selected from a set of subunits with the properties of mutual discriminability and substantially equivalent melting temperature. Constructing oligonucleotide tags from a plurality of oligonucleotide subunits permits the convenient and inexpensive formation of very large sets of oligonucleotide tags e.g. as described by Brenner et al, Proc. Natl. Acad. Sci., 97:1665-1670 (2000). Also, the use of oligonucleotide subunits permits enzymatic synthesis and/or attachment of oligonucleotide tags to polynucleotides, e.g. as described below and in Brenner and Williams, U.S. patent publication 2003/0049616. In one aspect, oligonucleotide tags comprise a plurality of oligonucleotide subunits. Such subunits may vary widely in length. In one aspect, the length of oligonucleotide subunits is in the range of from 2 to 18 nucleotides; in another aspect, the length of oligonucleotide subunits is in the range of from 2 to 8 nucleotides; and in another aspect the length of oligonucleotide subunits is in the range of from 2 to 5 nucleotides. A plurality of oligonucleotide subunits making up an oligonucleotide tag may also vary widely depending on their application. In one aspect, such plurality is a number in the range of 2 to 10; and in another aspect, such plurality is a number in the range of from 2 to 6. The size of a set of oligonucleotide subunits is usually smaller than the size of a set of oligonucleotide tags. Usually, a set of oligonucleotide subunits has a size in the range from 2 to 20; or in another embodiment, from 2 to 10 or in another embodiment, from 4 to 8. It is clear to one of ordinary skill that for subunit only two nucleotides in length that the size of a set of subunits would be smaller than that of subunits having greater lengths.

"Polymerase chain reactions" or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually the reaction is cycled through different temperatures optimized for each step in a thermal cycler instrument. Particular temperatures, durations at each step, and rates of change, between steps depend on many factor, well-known to those of ordinary skill in the art, e.g. exemplified by the references. McPherson et al, editors, PCR; A Practical Approach and PCR2: A Practical Approach (IRL Press, Oxfold, 1991 and 1995, respectively). For example, in a conventional PCR using Taq DNA polymerase, a double stranded target nucleic acid may be denatured at a temperature, >90°C., primers annealed at a temperature in the range 50-75° C., and primers extended at a temperature in the range 72-78° C. The term "PCR" encompasses derivative forms of the reaction, including but not limited to, RT-PCR, real-time PCR nested PCR, quantitative PCR, multiplexed PCR, and the like. Reaction volumes range from a few hundred nanoliters e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified e.g. Tecott et al, U.S. Pat. No. 5,168,038, which patent is incorporated herein by reference "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30:1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested amplicon. "Multiplexed PCR" means PCR wherein multiple target sequences (or a single target sequence and one or more reference sequence) are simultaneously carried out in the same reaction mixture, e.g. Bernard et al, Anal. Biochem., 273:221-228 (1999)(two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequences may be endogenous or exongenous to a sample or specimen, and in the latter case, may comprise one or more competitor templates. Typical endogenous reference sequences include segments of transcripts of the following genes: β-actin, GAPDH, β$_2$-microglobulin, ribosomal RNA, and the like. Techniques for quantitative PCR are well-known to those of ordinary skill in the art, as exemplified in the following references that are incorporated by reference. Freeman et al, Biotechniques, 26:112-126 (1999); Becker-Andre et al, Nucleic Acids Research, 17:9437-9447 (1989); Zimmerman et al, Biotechniques, 21:268-279 (1996); Diviacco et al, Gene, 122:3013-3020 (1992); Becker-Andre et al, Nucleic Acids Research, 17:9437-9446 (1989); and the like.

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individual, within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g. an allele present in a population at a frequency of fifty percent or greater.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking. Hoogsteen or reverse Hoogsteen types of base pairing, or the like. Such monomers and their internucleotide linkages may be naturally occurring or may be analogs thereof, e.g. naturally occurring or non-naturally occurring analogs. Non-naturally occurring analogs may include PNAs, phosphorothioate internucleosides linkages, bases containing linking groups permitting the attachment of labels, such as fluorophores, or haptens and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidie linkages, sugar moities, or bases at any or some positions. Polynucleotides typically range in size from a few monomeric units, e.g. 5-40, when they are usually referred to as "oligonucleotides", to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxcytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss New York 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleoside linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides. Preferably, primers have a length in the range of from 18 to 24 nucleotides.

"Readout" means a parameter, or parameters, which are measured and/or detected that can be converted to a number or value. In some contexts, readout may refer to an actual numerical representation of such collected or recorded data. For example, a readout of fluoresent intensity signals from a microarray is the address and fluorescene intensity of a signal being generated at each hybridization site of the microarray; thus, such a readout may be registered or stored in various ways, for example, as an image of the microarray, as a table of numbers, or the like. A readout is "digital" when the number or value is obtained by a counting process, e.g. determining a value by counting on a microarray the number of hybridization from which signals are being generated (as distinguished from those sites not generating signals).

"Sample" is used in at least two different contexts in connection with the invention. In one context, "sample," or equivalently "test sample," means a quantity of material from a biological, environmental, medical, or patient source in which detection or measurement of target polynucleotides or nucleic acids is sought. It may include a specimen or culture (e.g., microbiological cultures), or other types of biological or environmental samples. A test sample may include a specimen of synthetic origin. Biological test samples may be animal, including human, fluid, solid (e g., stool) or tissue, as well as liquid and solid food and feed products and ingredients such as dairy items, vegetables, meat and meat by-products, and waste. Biological test samples may include materials taken from a patient including, but not limited to cultures, blood, saliva, cerebral spinal fluid, pleural fluid, milk, lymph, sputum, semen, needle aspirates, and the like. Biological test samples may be obtained from all of the various families of domestic animals, as well as feral or wild animals, including, but not limited to, such animals as ungulates, bear, fish rodents, etc. Environmental test samples include environmental material such as surface matter, soil, water and industrial samples, as well as test samples obtained from food and dairy processing instruments, apparatus, equipment utensils, disposable and non-disposable items. These examples are not to be construed as limiting the sample types applicable to the present invention. In the other context, sample refers to a sample of selectable probes isolated from a reaction mixture. That is, it refers to a subset or subpopulation of selectable probes isolated from a reaction mixture that is representative of the full set or population of selectable probes formed in the reaction mixture.

Single-stranded or double-stranded DNA populations according to the present invention may refer to any mixture of two or more distinct species of single-stranded DNA or double-stranded DNA, which may include DNA representing genomic DNA, genes, gene fragments, oligonucleotides, PCR products, expressed sequence tags (ESTs), or nucleotide sequences corresponding to known or suspected single nucleotide polymorphisms (SNPs), having nucleotide sequences that may overlap in part or not at all when compared to one another. The species may be distinct based on any chemical or biological differences, including differences in base composition, order, length, or conformation. The single-stranded DNA population may be isolated or produced according to methods known in the art, and may include single-stranded cDNA produced from a mRNA template, single-stranded DNA isolated from double-stranded DNA, or single-stranded DNA synthesized as an oligonucleotide. The double-stranded DNA population may also be isolated according to methods known in the art, such as PCR, reverse transcription, and the like. Generally, one of ordinary skill in the art recognize when DNA called for in a process is required to be in single stranded form or double stranded form, such as, when hybridizing a primer to a target polynucleotide or processing a polynucleotide with a restriction endonuclease, respectively. Where the single-stranded DNA population of the present invention is cDNA produced from a mRNA population, it may be produced according to methods known in the art. See, e.g., Maniatis et al. In a preferred embodiment, a sample population of single-stranded poly(A)+ RNA may be used to produce corresponding cDNA in the presence of reverse transcriptase, oligo-dT primer(s) and dNTPs. Reverse transcriptase may be any enzyme that is capable of synthesizing a corresponding cDNA from an RNA template in the presence of the appropriate primers and nucleotide triphosphates. In a preferred embodiment, the reverse transcriptase may be from avian mycloblastosis virus (AMV), Moloney murine leukemia virus (MMuLV) or Rous Sarcoma Virus (RSV), for example, and may be thermal stable enzyme (e.g., hTth DNA polymerase).

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with; for example, wells, raised regions, pins, etched trenches, or the like. According to other embodiments, the solid support(s) will take the form of beads, resins gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contract, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as Van der Waal forces, hydrogen bonding, base-stacking interactions, ionic and hydrophobic interactions, and the like, dominate the interaction of the molecules.

"$T_m$" is used in reference to "melting temperature." Melting temperature is the temperature at which a population of double-stranded nucleic acid molecules becomes half dissociated into single strands. Several equations for calculating the Tm of nucleic acids are well known in the art. As indicated by standard references, a simple estimate of the tm value may be calculated by the equation. Tm =81.5+0.41 (%G+C), when a nucleic acid is in aqueous solution at 1 M NaCl (see e.g., Anderson and Young, Quantitative Filter Hybridization, in Nucleic Acid Hybridization (1985). Other references (e.g., Allawi H. T. & SantaLucia, J., Jr., Biochemistry 36, 10581-94 (1997)) include alternative methods of computation which take structural and environmental, as well as sequence characteristics into account for the calculation of Tm.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method of forming closed double stranded DNA circles from a plurality of target polynucleotides in a sample, the method comprising the steps of:

providing one or more selection oligonucleotides for each of the plurality of target polynucleotide so that each of such one or more selection oligonucleotides has a phosphorylated 5' end and is capable of specifically annealing at the same time to two non-contiguous sites on its respective target polynucleotide whenever present in the sample to form a circular complex therewith comprising a free 5' strand and a free 3' strand; and combining in a reaction mixture the sample, nucleoside triphosphates, and the selection oligonucleotides under conditions such that the following enzymatic activities are present: (i) a 5' flap endonuclease activity, (ii) a DNA polymcrasc lacking strand displacement activity, (iii) a 3' single stranded exonuclease activity, and (iv) a ligase activity, wherein for each circular complex any free 3'strand is digested to form an extendable duplex that is extended by the DNA polymerase activity to the free 5' strand of the circular complex, any free 5' strand of the circular complex adjacent to an extended extendable duplex is cleaved to form a first nick, the annealed selection oligonucleotide is extended from a 3' end along the circular complex to a 5'end of the selection oligonucleotide to form a second nick, and the first and second nicks are ligated to form a closed double stranded DNA circle.

2. The method of claim 1 wherein said 5' flap endonuclease activity, said DNA polymcrasc activity, said 3' single stranded exonuclease activity, and said ligase activity are provided by a FEN-1 nuclease, a T4 DNA polymerase, and a ligase.

3. The method of claim 1 further including the step of linearizing said closed double stranded DNA circle.

4. The method of claim 3 wherein said selection oligonucleotides include a restriction site and wherein said step of linearizing includes treating said closed double stranded DNA circle with an endonuclease recognizing the restriction site.

5. The method of claim 1 further including the step of treating said reaction mixture with nucleases to destroy oligonucleotides or polynucleotides that are not closed double stranded DNA circles.

6. The method of claim 1 further including the step of amplifying said closed double stranded DNA circle.

7. The method of claim 6 wherein said step of amplifying includes linearizing said closed double stranded DNA circle to form a linear double stranded DNA and amplifying the linear double stranded DNA in a polymerase chain reaction.

8. The method of claim 6 wherein said step of amplifying includes rolling circle amplification.

9. The method of claim 1 wherein said one or more selection oligonucleotides are a plurality of selection oligonucleotides.

10. The method of claim 9 wherein said plurality of selection oligonucleotides includes between 10 and 1000 selection oligonucleotides 11. The method of claim 10 wherein said plurality of selection oligonucleotides includes between 10 and 100 selection oligonucleotides.

12. The method of claim 1 wherein said target polynucleotides are random fragments.

13. A method of amplifying a plurality of target polynucleotides in a sample, the method comprising the steps of:
providing one or more selection oligonucleotides for each of the plurality of target polynucleotide so that each of such one or more selection oligonucleotides has a phosphorylated 5' end and is capable of specifically annealing at the same time to two non-contiguous sites on its respective target polynucleotide whenever present in the sample to form a circular complex therewith comprising a free 5' strand and a free 3' strand;
combining in a reaction mixture the sample, nucleoside triphosphates, and the selection oligonucleotides under conditions such that the following enzymatic activities are present: (i) a 5' flap endonuclease activity, (ii) a DNA polymerase lacking strand displacement activity, (iii) a 3' single stranded exonuclease activity, and (iv) a ligase activity, wherein for each circular complex any free 3'strand is digested to form an extendable duplex that is extended by the DNA polymerase activity to the free 5' strand of the circular complex, any free 5' strand of the circular complex adjacent to an extended extendable duplex is cleaved to form a first nick, the annealed selection oligonucleotide is extended from a 3' end along the circular complex to a 5'end of the selection oligonucleotide to form a second nick, and the first and second nicks are ligated to form a closed double stranded DNA circle;

treating the reaction mixture with nucleases to destroy oligonucleotides and polynucleotides that are not closed double stranded DNA circles;
linearizing the closed double stranded DNA circle to form a linear double stranded DNA; and
amplifying the linear double stranded DNA in a polymerase chain reaction.

14. The method of claim 13 wherein said plurality of selection oligonucleotides includes between 10 and 1000 selection oligonucleotides.

15. The method of claim 14 wherein said plurality of selection oligonucleotides includes between 10 and 100 selection oligonucleotides.

16. The method of claim 15 wherein said plurality of selection oligonucleotides includes between 10 and 50 selection oligonucleotides.

17. The method of claim 13 wherein said target polynucleotides each have a length in the range of from 50 to 2000 nucleotides.

18. The method of claim 13 wherein said 5' flap endonuclease activity, said DNA polymerase activity, said 3' single stranded exonuclease activity, and said ligase activity are provided by a FEN-1 nuclease, a T4 DNA polymerase, and a ligase.

19. The method of claim 18 wherein said ligase is selected from the group consisting of Taq DNA ligase, *E. coli* DNA ligase, and T4 ligase.

20. A method of forming closed double stranded DNA circles from a plurality of target polynucleotides in a sample, the method comprising the step of:
combining in a reaction mixture the sample, one or more selection oligonucleotides for each of the plurality of target polynucleotides and nucleoside triphosphates, each of the one or more selection oligonucleotides having a phosphorylated 5' end and a nuclease resistant 3' end and specifically annealing at the same time to two non-contiguous sites on its respective target polynucleotide whenever present in the sample to form a circular complex therewith comprising a free 5' strand and a free 3' strand, and the reaction mixture having conditions such that the following enzymatic activities are present: (i) a 5' flap endonuclease activity, (ii) a DNA polymerase lacking strand displacement activity. (iii) a 3' single stranded exonuclease activity, and (iv) a ligase activity, such that for each circular complex any free 3'strand is digested to form an extendable duplex that is extended by the DNA polymerase activity to the free 5' strand of the circular complex, any free 5' strand of the circular complex adjacent to an extended extendable duplex is cleaved to form a first nick, the annealed selection oligonucleotide is extended from a 3' end along the circular complex to a 5'end of the selection oligonucleotide to form a second nick, and the first and second nicks are ligated to form a closed double stranded DNA circle.

21. The method of claim 20 wherein said 5' flap endonuclease activity, said DNA polymerase activity, said 3' single stranded exonuclease activity, and said ligase activity are provided by a FEN-1 nuclease, a T4 DNA polymerase, and a ligase.

* * * * *